United States Patent [19]

Alaimo et al.

[11] Patent Number: 4,716,168

[45] Date of Patent: Dec. 29, 1987

[54] IMIDAZO(4,5-f)QUINOLINES USEFUL AS IMMUNOMODULATING AGENTS

[75] Inventors: Robert J. Alaimo; Jon A. Andersen, both of Norwich, N.Y.

[73] Assignee: Norwich Eaton Pharmaceuticals, Inc., Norwich, N.Y.

[21] Appl. No.: 858,093

[22] Filed: Apr. 29, 1986

Related U.S. Application Data

[63] Continuation of Ser. No. 689,628, Jan. 8, 1985, abandoned.

[51] Int. Cl.$^4$ .................. A61K 31/415; C07D 471/04
[52] U.S. Cl. ................................. 514/293; 514/287; 546/82; 546/64; 544/126; 544/361; 534/802
[58] Field of Search ................ 546/82, 64; 544/126, 544/361; 534/802; 514/293, 287

[56] References Cited

U.S. PATENT DOCUMENTS 3,868,378  2/1975  Spencer et al. ................ 260/289 R
3,878,206  4/1975  Spencer et al. ............ 260/247.5 EP
3,919,238  11/1975  Spencer et al. .............. 260/288 CF

OTHER PUBLICATIONS

Goodman and Gilman. The Pharmacological Basis of Therapeutics 6th ed., p. 28.

Alaimo, R. J., C. F. Spencer, J. B. Sheffer, R. J. Storrin, C. J. Hatton and R. E. Kohls, "Imidazol[4,5-f]Quinolines, 4, Synthesis and Anthelmintic Activity of a Series of Imidazo[4,5-f]Quinolin-9-ols", Journal of Medicinal Chemistry, vol. 21, No. 3, (1978), pp. 298–300.

Spencer, C. F., H. R. Snyder, Jr., H. A. Burch and C. J. Hatton, "Imidazo[4,5-f]Quinolines. 2. A Series of 9-(-Substituted Amino)Imidazo[4,5-f]Quinolines as Antitapeworm Agents", Journal of Medicinal Chemistry, vol. 20, No. 6, (1977), pp. 829–833.

Snyder, H. R., Jr., C. F. Spencer and R. Freedman, "Imidazo[4,5-f]Quinolines III: Antibacterial 7-Methyl-9-(substituted Arylamino)Imidazo[4,5-f]Quinolines", Journal of Phamaceutical Sciences, vol. 66, No. 8 (Aug., 1977), pp. 1204–1206.

Ishiwata, S. and Y. Shiokawa, "Synthesis of Benzimidazoles and Related Compounds. II. Synthesis of 3H-Imidazo[4,5-f]– and 1H-Imidazo[5,4-g]quinolines", Chemical Pharmaceutical Bulletin, vol. 17, No. 12, (1969), pp. 2455–2460.

Spencer, C. F., H. R. Snyder, Jr. and R. J. Alaimo, "9-Chloro– (or Hydroxy)–2 and/or 7-Substituted-Imidazo[4,5-f]Quinolines (I)", Journal of Heterocyclic Chemistry, vol. 12, No. 6 (Dec., 1975), pp. 1319–1321.

Primary Examiner—Henry R. Jiles
Assistant Examiner—J. Richter
Attorney, Agent, or Firm—Milton B. Graff, IV; Kim William Zerby; Jack D. Schaeffer

[57] ABSTRACT

The present invention involves compounds of the class of imidazo[4,5-f]quinolines and methods for enhancing the immune response system of mammals which comprises systemically administering to mammals having a depressed immune function an effective but nontoxic amount of a composition comprising such a compound.

21 Claims, No Drawings

IMIDAZO(4,5-F)QUINOLINES USEFUL AS IMMUNOMODULATING AGENTS

This is a continuation of application Ser. No. 689,628, filed on Jan. 8, 1985, now abandoned.

TECHNICAL FIELD

The present invention relates to compounds and compositions which are useful as immunomodulating agents, and to the treatment of a host to increase the function of the immune system of the host.

BACKGROUND OF THE INVENTION

A state of immunosuppression of a host is often an undesired side effect of drug treatment; such an effect is commonly found as the result of cancer chemotherapy involving antineoplastic agents. Such a suppression of the immune system lessens the body's own natural defense mechanisms and enhances the probability of infection.

As used herein, an immunomodulator is an agent which enhances a depressed immune function of a host mammal. Immune function is defined as the development and expression of humoral (antibody-mediated) immunity, cellular (t-cell-mediated) immunity, or macrophage and granulocyte mediated resistance. It includes agents acting directly on the cells involved in the expression of immune response, or on cellular or molecular mechanisms which act to modify the function of cells involved in immune response. Augmentation of immune function may result from the action of an agent to abrogate suppressive mechanisms by negative-feedback influences endogenous or exogenous to the immune system. Thus, immunomodulators have diverse mechanisms of action. Despite the diversity of cell site of action and biochemical mechanism of action of immunomodulators, their applications are essentially the same; that is, to enhance host resistance.

The principal protective function of the immune system relates to resistance to invasion by pathogens, including viruses, rickettsia, mycoplasma, bacteria, fungi and parasites of all types. Thus, improvement of immune response, particularly when depressed, would be expected to improve resistance to infection or infestation by any of the above pathogens. An immunomodulator alone or in combination with anti-infective therapy can be applied to any and all infectious diseases.

Another protective function of the immune system is thought to be resistance to malignant cell development as in cancer. The use of immunomodulators can be used in cancer treatment to enhance tumor rejection and to inhibit tumor recurrences following other forms of therapy.

Each of the protective functions of the immune system can be modified by therapy with immunomodulators alone or in combination with other agents employed to improve resistance or to kill the invading pathogen. In addition, specific resistance can be augmented by use of immunomodulators in conjunction with some form of antigen as in a vaccine employing, for example, virus, tumor cells, etc. This could induce specific immunity or tolerance. Use of immunomodulators may be either therapeutic or prophylactic; the latter particularly in aging where infection and cancer are more common, or where immunosuppression is induced by drugs, trauma, or surgery. The timing of administration and routes are variable and may be critical in determining whether a positive response results.

Certain imidazo[4,5-f]quinolines are known, and it has been disclosed that some of these compounds have antibacterial or anthelminitic activity. The following references disclose certain imidazo[4,5-f]quinolines and methods of synthesizing them and are hereby incorporated by reference: U.S. Pat. No. 3,868,378 issued to Spencer and Alaimo on Feb. 25, 1975; U.S. Pat. No. 3,878,206 issued to Spencer and Snyder on Apr. 15, 1975; U.S. Pat. No. 3,919,238 issued to Spencer and Snyder on Nov. 11, 1975; Ishiwata, S., and Y. Shiokawa, "Synthesis of Benzimidazoles and Related Compounds. II. Syntheses of 3H-Imidazo[4,5-f]- and 1H-Imidazo-[5,4-g]quinolines", *Chemical Pharmaceutical Bulletin*, Vol. 17 (1969), pp. 2455–2460; Spencer, C. F., H. R. Snyder, Jr., and R. J. Alaimo, "9-Chloro-(or hydroxy)-2 and/or 7-substituted-imidazo[4,5-f]quinolines (1)", *Journal of Heterocyclic Chemistry*, Vol. 12, No. 6(December, 1975), pp. 1319–1321; Spencer, C. F., H. R. Synder, Jr., H. A. Burch, and C. J. Hatton, "Imidazo[4,5-f]quinolines. 2. A Series of 9-(Substituted amino)imidazo[4,5-f]quinolines as Antitapeworm Agents", *Journal of Medicinal Chemistry*, Vol. 20, No. 6 (1977), pp. 829–833; Snyder, H. R., Jr., C. F. Spencer, and R. Freedman, "Imidazo[4,5-f]quinolines III: Antibacterial 7-methyl-9-(substituted Arylamino)imidazo[4,5-f]quinolines", *Journal of Pharmaceutical Sciences*, Vol. 66, No. 8 (August 1977), pp. 1204–1206; Alaimo, R. J., C. F. Spencer, J. B. Scheffer, R. J. Storrin, C. J. Hatton, and R. E. Kohls, "Imidazo[4,5-f]quinolines. 4. Synthesis and Anthelmintic Activity of a Series of Imidazo[4,5-f]quinolin-9-ols", *Journal of Medicinal Chemistry*, Vol. 21, No. 3 (1978), pp. 298–300.

SUMMARY OF THE INVENTION

It is an object of the present invention to provide a method of enhancing the immune response system in mammals.

It is a further object of this invention to provide such enhanced immune response system to mammals in which such system has been suppressed.

It is also an object of this invention to provide novel compounds which enhance the immune response system in mammals.

It is also an object of this invention to provide pharmaceutical compositions which enhance the immune response system in mammals.

DETAILED DESCRIPTION OF THE INVENTION

In one of its aspects, the present invention is a method for enhancing the immune response system of mammals which comprises systemically administering to mammals having depressed immune function an effective but nontoxic amount of a composition comprising certain imidazo[4,5-f]quinolines as immunomodulating agents. The imidazo[4,5-f]quinolines found to be useful as immunomodulating agents conform to the chemical structure:

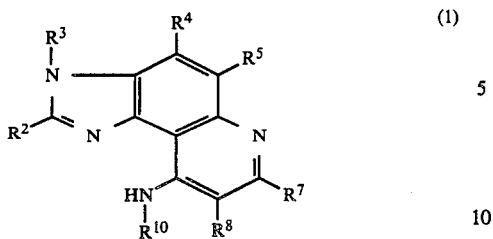
(1)

wherein $R^2$ is H, straight or branched chain lower alkyl, aryl, substituted aryl, heteroaryl, or trihalomethyl; $R^3$ is H or straight or branched chain lower alkyl; $R^4$ and $R^5$ are H or straight or branched chain lower alkyl, or $R^4$ and $R^5$ are connected lower alkylene derivatives; $R^7$ is H, straight or branched chain lower alkyl, aryl, substituted aryl, heteroaryl, (lower)alkoxycarbonyl, or trihalomethyl; $R^8$ is H, lower alkyl, or (lower)alkoxycarbonyl, or $R^7$ and $R^8$ are connected lower alkylene derivatives; and $R^{10}$ is H, straight or branched chain alkyl, cycloalkyl, aryl, substituted aryl, naphthyl, heteroaryl, substituted heteroaryl, arylalkyl or substituted arylalkyl;

and salts and/or hydrates thereof (Compounds A). Preferred compounds useful in the present invention are the hydrochloride salts of Compounds A.

Preferred imidazo[4,5-f]quinolines useful in the present invention include compounds which conform to the chemical structure of Compounds A hereinabove, but wherein $R^{10}$ is phenyl or mono-, di- or trisubstituted phenyl. More preferred are such imidazo[4,5-f]quinolines wherein said substituted phenyl is substituted with groups such as halo, nitro, cyano, hydroxy, $C_1$–$C_{20}$ straight or branched chain alkyl, cycloalkyl, $C_1$–$C_{20}$ straight or branched chain alkoxy, aryl, trihalomethyl, aryloxy, arylalkyloxy, cycloalkyloxy, cycloalkylalkyloxy, phenylazo, piperidyl, morpholinyl, pyrrolidyl, alkylpiperazinyl, carboxylic acid and carboxylic acid esters, alkylthio, carboxyalkyl and their esters, hydroxyalkyl benzoyl, acetyl, propionyl, 2-dialkylaminoethoxy, 3,4-dimethylenedioxy, and/or mono- or disubstituted aminos substituted with H, lower alkyl, hydroxyalkyl, and/or alkanoyl. More preferred still are such compounds wherein said substituted phenyl is substituted with groups such as halo, cyano, $C_1$–$C_{12}$ straight or branched chained alkyl, $C_1$–$C_{10}$ straight or branched chained alkoxy, and/or mono- or disubstituted aminos substituted with H, lower alkyl, hydroxyalkyl, and/or alkanoyl. Especially preferred are such compounds wherein said substituted groups are 4-cyano, 3,4-difluoro, 4-n-butyl, 4-methoxy, or 4-N-methylacetamido.

Preferred imidazo[4,5-f]quinolines used in the present invention include compounds which conform to the chemical structure of Compounds A hereinabove, but wherein $R^2$ is H, phenyl, furanyl, thiazoyl, and thienyl; especially preferred are such compounds wherein $R^2$ is H.

Preferred imidazo[4,5-f]quinolines useful in the present invention include compounds which conform to the chemical structure of Compounds A hereinabove, but wherein $R^3$ is H. When $R^3$ is H in compounds which conform to chemical structure (1) hereinabove, chemical structure (a):

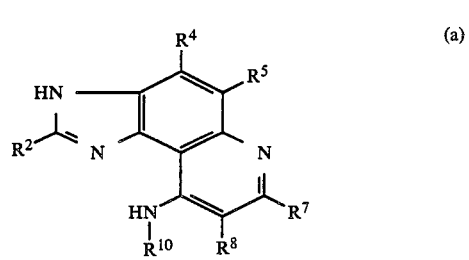
(a)

is equivalent to chemical structure (b):

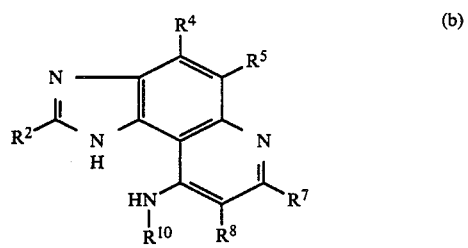
(b)

In order to conform to usual convention, chemical structures analogous to (b) will be used herein and will be understood to include those analogous to (a) also.

Preferred imidazo[4,5-f]quinolines useful in the present invention include compounds which conform to the chemical structure of Compounds A hereinabove, but wherein $R^4$ is H.

Preferred imidazo[4,5-f]quinolines useful in the present invention include compounds which conform to the chemical structure of Compounds A hereinabove, but wherein $R^5$ is H.

Preferred imidazo[4,5-f]quinolines useful in the present invention include compounds which conform to the chemical structure of Compounds A hereinabove, but wherein $R^8$ is H.

Preferred imidazo[4,5-f]quinolines useful in the present invention include compounds which conform to the chemical structure of Compounds A hereinabove, but wherein $R^7$ is H, methyl, phenyl, or furanyl; especially preferred are such compounds wherein $R^7$ is methyl; also especially preferred are such compounds wherein $R^7$ is phenyl.

Preferred imidazo[4,5-f]quinolines useful in the present invention include compounds which conform to the chemical structure of Compounds A hereinabove, but wherein such compounds include any combination of the preferred groups of $R^2$, $R^3$, $R^4$, $R^5$, $R^7$, $R^8$, and $R^{10}$ disclosed hereinabove.

Especially preferred imidazo[4,5-f]quinolines useful as immunomodulating agents include compounds which conform to the following chemical structures:

4-[[7-methyl-1H-imidazo[4,5-f]quinolin-9-yl]amino]benzonitrile hydrochloride hydrate

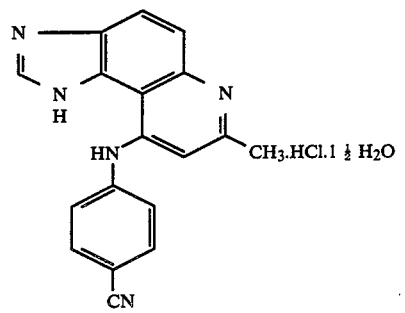
(3)

N-[3,4-difluorphenyl]-7-phenyl-1H-imidazo[4,5-f]quinolin-9-amine hydrochloride

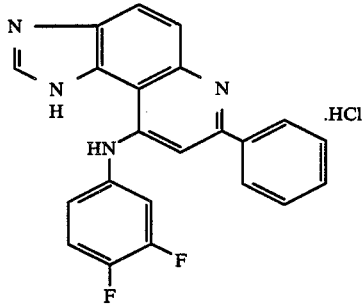
(4)

N-(3,4-difluorophenyl)-1H-imidazo[4,5-f]quinolin-9-amine hydrochloride

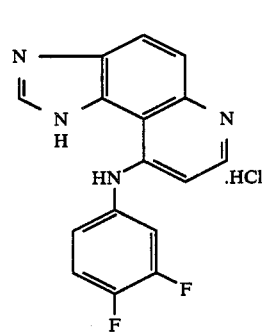
(5)

4-[[7-phenyl-1H-imidazo[4,5-f]quinolin-9-yl]amino]benzonitrile hydrochloride hydrate

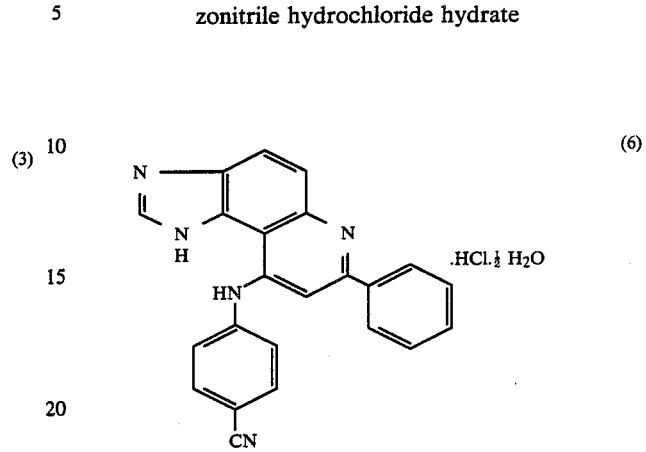
(6)

2-(2-furanyl)-N-(4-methoxypheny)-7-methyl-1H-imidazo[4,5-f]quinolin-9-amine hydrochloride hydrate

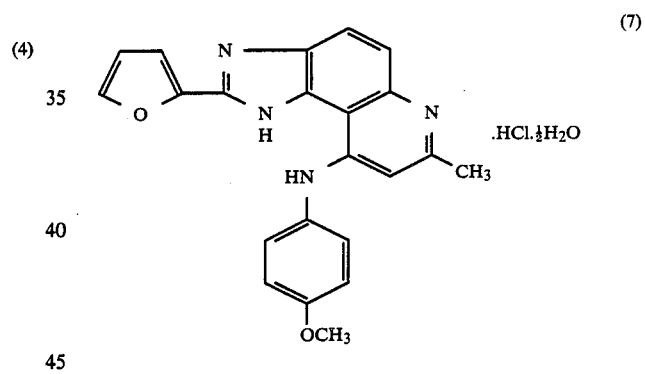
(7)

9-[p-(N-methylacetamido)anilino]-7-methyl-1H-imidazo[4,5-f]quinoline hydrochloride hydrate

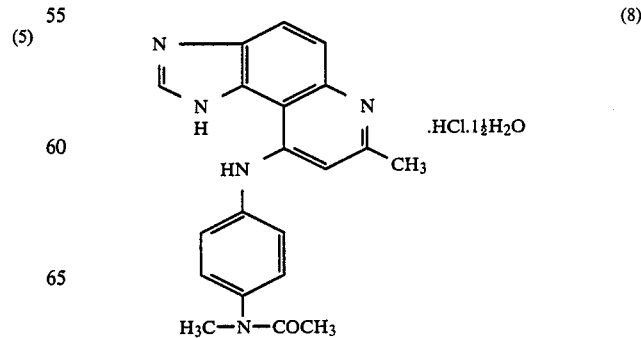
(8)

9-(p-anisidino)-7-methyl-2-phenyl-1H-imidazo[4,5f-]quinoline hydrochloride hydrate

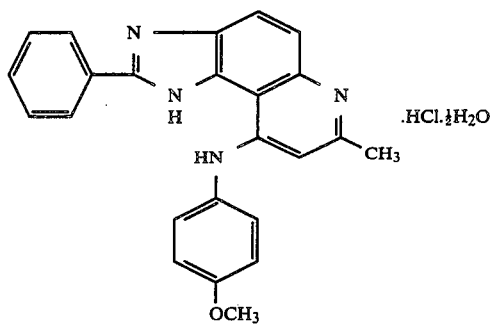

(9)

9-(p-butylanilino)-7-phenyl-1H-imidazo[4,5-f]quinoline hydrochloride

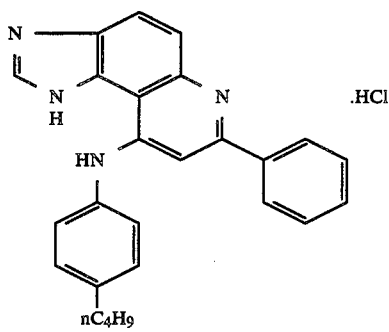

(10)

The immunomodulating activity of compounds of the present invention can be demonstrated using the test method set forth in the following reference: Bicker, V., G. Hebold, A. E. Ziegler and W. Maus, "Animal Experiments on the Compensation of the Immunosuppressive Action of Cyclophosphamide by 2-(-2 Cyanaziridinyl-(1)-)-2-(-2-carbamoyl-aziridinyl-(1))-propane BM 12.531", Experimental Pathology Bd., Vol. 15, No. 1 (1978), pp. 49–62. The test method is based on the use of an immunosuppressing agent (generally cyclophosphamide) to depress the bacterial resistance of a host mammal (generally Swiss-Webster mice). The test compound is given to some of the mice which are then given a dose of a pathogenic organism (generally Pseudomonas aeruginosa). The survival of the animals treated with the test compound is compared to those not treated.

TEST METHOD

A. Animals

Mice were obtained from Charles River Breeding Laboratories, Wilmington, Mass., and were Swiss-Webster outbred CD-1 females weighting 14–16 g on arrival. They weighed 20–25 g when used. The desired number of mice (generally 20–40) were divided into two groups, a control group and an experimental group, for each test. Five mice were housed per stainless steel cage (17.5×24.5×12.5 cm). Animals were given Purina Lab Chow and water ad libitum. Room temperature was 21°–24° C., relative humidity 25–50%. Lighting was on from 6 AM–6 PM.

B. Organism

*Pseudomonas aeruginosa* (Ps-44) was from the stock collection of Eaton Laboratories. It was grown on Trypticase Soy Agar, harvested in 10% skim milk, distributed in disposable tubes and stored at −73° C. For animal inoculation the suspension was thawed, incubated in Trypticase Soy Broth 18 hours at 37° C. and washed three times in phosphate buffered saline (PBS), pH 7.4, before being appropriately diluted in PBS for use. Estimations of cell populations were made on a Bausch and Lomb Spectronic 20 colorimeter and viable plate counts done for confirmation. *Escherichia coli* (Es-90) was maintained on Brain Heart agar slants at 4° C.

C. Drugs

Cyclophosphamide (e.g., Cytoxan, Mead Johnson) was purchased commercially. Cyclophosphamide (CY) and experimental compounds were diluted to desired concentrations in sterile, non-pyrogenic saline from Abbott Laboratories, N. Chicago, Ill. 60064.

D. Mouse Infection

All mice in both the control and experimental groups were initially infected with 0.2 ml containing $1 \times 10^6$ *Pseudomonas aeruginosa* intravenously (i.v.) on Day 0.

E. Screening

The mice in both the control and experimental groups are immunosuppressed by injecting either 100 or 150 mg/kg CY 4 days (Day -4) before *P. aeruginosa* challenge ($1 \times 10^6$ cells). Experimental compound was given subcutaneously (s.c.) to mice in the experimental group only on Days -4 and -2. The dose level was normally 80 mg/kg. Some experimental compounds were tested at lower levels. The biological activity is reported as percent protection afforded by the experimental compound at a given dose. Percent protection is calculated as follows:

% Protection = $\frac{\text{\% dead in control group} - \text{\% dead in experimental group}}{\text{\% dead in control group}} \times 100$

EXAMPLES I-CLI

Experimental compounds having the following chemical structure were tested for immunomodulating activity according to the above test method:

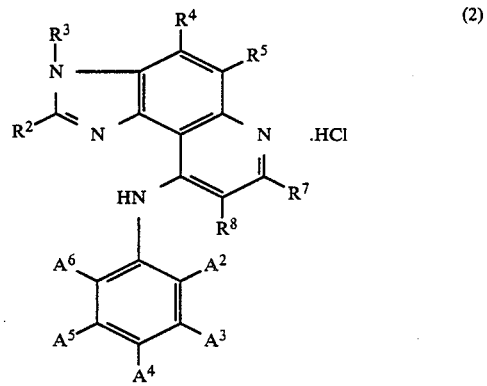

(2)

wherein $R^4 = R^5 = A^6 = H$.

The results of the tests are provided in Table I:

TABLE I

| EXAMPLE | R² | R³ | R⁷ | R⁸ | A² | A³ | A⁴ | A⁵ | Protection (%) |
|---|---|---|---|---|---|---|---|---|---|
| I | H | H | —CH₃ | H | H | H | —OCH₃ | H | 98 |
| II | H | H | —CH₃ | H | H | H | H | H | 77 |
| III | H | H | —CH₃ | H | H | H | —OCH₂CH₃ | H | 100 |
| IV | H | H | —CH₃ | H | H | H | —N(CH₃)₂ | H | 100 |
| V | H | H | —CH₃ | H | H | H | —OH | H | 79 |
| VI | H | H | —CH₃ | H | H | H | —Cl | H | 100 |
| VII | H | H | —CH₃ | H | H | —Cl | —Cl | H | 100 |
| VIII | H | H | —CH₃ | H | H | —OCH₃ | —OCH₃ | H | 75 |
| IX | H | H | —CH₃ | H | H | H | H | H | 71 |
| X | H | H | —CH₃ | H | —OCH₃ | H | —N(CH₃)₂ | H | 100 |
| XI | H | H | —CH₃ | H | H | —Cl | —N(CH₃)₂ | H | 95 |
| XII | H | H | —CH₃ | H | —OCH₂CH₃ | H | H | —OCH₂CH₃ | 100 |
| XIII | H | H | —CH₃ | H | H | H | F | H | 100 |
| XIV | H | H | —CH₃ | H | H | H | —O(CH₂)₃CH₃ | H | 100(a) |
| XV | H | H | —CH₃ | H | H | H | —Br | H | 100 |
| XVI | H | H | —CH₃ | H | H | —Cl | —N(CH₃)₂ | H | 100 |
| XVII | H | H | —CH₃ | H | H | H | —CH₃ | H | 100 |
| XVIII | H | H | —CH₃ | H | H | —OCH₃ | H | H | 100 |
| XIX | H | H | —CH₃ | H | H | H | —NHCOCH₃ | H | 79 |
| XX | H | H | —CH₃ | H | H | H | H | —CH₃ | 82 |
| XXI | H | H | —CH₃ | H | H | H | —OCH₃ | —OCH₃ | 100 |
| XXII | H | H | —CH₃ | H | —Cl | H | —Cl | —Cl | 91 |
| XXIII | H | H | —CH₃ | H | —OCH₃ | H | —OCH₃ | —OCH₃ | 100 |
| XXIV | H | H | —CH₃ | H | —OCH₃ | H | —OCH₃ | H | 83 |
| XXV | H | H | —CH₃ | H | —OCH₃ | H | —OCH₃ | H | 100 |
| XXVI | H | H | —CH₃ | H | H | —OCH₂CH₃ | —OCH₂CH₃ | H | 100 |
| XXVII | H | H | —CH₃ | H | H | —OCH(CH₃)₂ | —OCH(CH₃)₂ | H | 100 |
| XXVIII | H | H | —CH₃ | H | H | H | —OC₆H₅ | H | 80 |
| XXIX | H | H | H | H | H | H | —N(CH₃)COCH₃ | H | 100(a) |
| XXX | —C₆H₅ | H | —CH₃ | H | H | H | —OCH₃ | H | 100 |
| XXXI | H | H | —CH₂CH₃ | H | H | H | —OCH₃ | H | 100 |
| XXXII | H | H | —CH₃ | H | —OCH₃ | H | H | H | 100 |
| XXXIII | H | H | —CH₃ | H | —OCH₃ | H | —OCH₃ | H | 100(g) |
| XXXIV | H | H | —CH₃ | H | H | H | —NHCH₃ | H | 73 |
| XXXV | H | H | —C₆H₅ | H | H | H | —NH₂ | H | 100 |
| XXXVI | H | H | —CH₃ | H | H | H | —OCH₃ | H | 64(b) |
| XXXVII | H | H | —CH₃ | H | H | —OCH₂CH₃ | —OCH₂CH(CH₃)₂ | H | 100 |
| XXXVIII | H | H | —CH₃ | H | H | H | —CO₂CH₂CH₃ | H | 100 |
| XXXIX | H | H | —CH₃ | H | H | H | —COC₆H₅ | H | 87 |
| XL | H | H | —CH₃ | H | —OCH₃ | H | H | —OCH₂CH₃ | 100 |
| XLI | H | H | —CH₃ | H | —OCH₃ | H | H | —COCH₃ | 100 |
| XLII | H | H | —CH₃ | H | —OCH₃ | —COCH₃ | —OCH₃ | —OCH₃ | 100 |
| XLIII | H | H | —CH₃ | H | H | H | —Cl | H | 92 |
| XLIV | H | H | —CH₃ | H | H | H | —COCH₂CH₃ | —OCH₂CH₃ | 100(a) |
| XLV | —CH₃ | H | —CH₃ | H | H | H | —CH(CH₂)₂CH₃ | H | 100 |
| XLVI | H | H | —CH₃ | H | H | H | —CH₂CH₂OH | H | 93 |
| XLVII | H | H | —CH₃ | H | H | H | —OCH₃ | H | 100 |
| XLVIII | H | H | —CH₃ | H | H | —(CH₂)₃CH₃ | —SCH₃ | H | 93 |
| XLIX | H | H | —CH₃ | H | H | H | —OCH₂(CH₂)₂CH₃ | H | 100 |
| L | H | H | —CH₃ | H | H | —Cl | —O—CH₂—O— | | 100 |
| LI | H | H | —CH₃ | H | H | H | H | H | 93 |
|  | H | H | —CH₃ | H | H | H | —CH₂CH₃ | H | 93 |

TABLE I-continued

| EXAMPLE | $R^2$ | $R^3$ | $R^7$ | $R^8$ | $A^2$ | $A^3$ | $A^4$ | $A^5$ | Protection (%) |
|---|---|---|---|---|---|---|---|---|---|
| LII | H | H | —CH$_3$ | H | H | H | —N⟨piperidine⟩ | H | 100 |
| LIII | H | H | —CH$_3$ | H | H | H | —N⟨morpholine⟩ | H | 100 |
| LIV | H | H | —CH$_3$ | H | —OCH$_2$CH$_3$ | H | —OCH$_2$CH$_3$ | —OCH$_2$CH$_3$ | 77 |
| LV | H | H | —CH$_3$ | H | H | —O(CH$_2$)$_4$CH$_3$ | —O(CH$_2$)$_4$CH$_3$ | H | 100 |
| LVI | H | H | —CH$_3$ | H | H | H | —I | H | 100 |
| LVII | H | H | —CH$_3$ | H | H | H | —N⟨N-CH$_3$ piperazine⟩ | H | 100 |
| LVIII | H | H | —CH$_3$ | H | H | H | —N⟨pyrrolidine⟩ | H | 100 |
| LIX | H | H | —CH$_3$ | H | H | H | —N(CH$_3$)CH$_2$CH$_2$OH | H | 87 |
| LX | H | H | —CH$_3$ | H | H | —N(CH$_3$)$_2$ | —C$_6$H$_5$ | H | 100 |
| LXI | H | H | —CH$_3$ | H | H | H | —H | H | 100 |
| LXII | H | H | —CH$_3$ | H | H | —Cl | —N⟨morpholine⟩ | H | 100 |
| LXIII | H | H | —CH$_3$ | H | H | —Cl | —CH$_3$ | H | 93 |
| LXIV | H | H | —CH$_3$ | H | H | H | —COCH$_2$CH$_3$ | H | 100 |
| LXV | H | H | —CH$_3$ | H | H | —NO$_2$ | —CH$_3$ | H | 100 |
| LXVI | H | H | —CH$_3$ | H | H | —Cl | —F | H | 88 |
| LXVII | H | H | —CH$_3$ | H | H | —Cl | —N⟨NCH$_3$ piperidine⟩ | H | 100 |
| LXVIII | H | H | —CH$_3$ | H | H | —CF$_3$ | —H | H | 100 |
| LXIX | H | H | —CH$_3$ | H | —OCH$_3$ | H | —Cl | H | 100 |
| LXX | H | H | —C$_6$H$_5$ | H | H | H | —(CH$_2$)$_3$CH$_3$ | H | 100 |

TABLE I-continued

| EXAMPLE | R² | R³ | R⁷ | R⁸ | A² | A³ | A⁴ | A⁵ | Protection (%) |
|---|---|---|---|---|---|---|---|---|---|
| LXXI | H | H | —CH₃ | H | H | Cl | —N⟨⟩ (pyrrolidinyl) | H | 94 |
| LXXII | H | H | —CH₃ | H | H | —OCH₂CH₂CH(CH₃)₂ | —OCH₂CH₂CH(CH₃)₂ | H | 100 |
| LXXIII | H | H | —CH₃ | H | H | H | —OCH₂C₆H₅ | H | 100 |
| LXXIV | H | H | —CH₃ | H | —SCH₃ | —SCH₃ | H | H | 100 |
| LXXV | H | H | —CH₃ | H | H | H | —N=N—C₆H₅ | H | 100 |
| LXXVI | H | H | —CH₃ | H | —CH₃ | H | H | H | 79 |
| LXXVII | H | H | —CH₃ | H | —C₆H₅ | H | —CO₂H | H | 100 |
| LXXVIII | H | H | —CH₃ | H | —CH₃ | —CF₃ | —Cl | H | 100 |
| LXXIX | H | H | —CH₃ | H | H | H | —Cl | H | 100 |
| LXXX | H | H | —CH₃ | H | H | H | H | H | 89 |
| LXXXI | H | H | —CH₃ | H | H | —Cl | —Cl | H | 78 |
| LXXXII | H | H | —CH₃ | H | H | —Cl | —OH | H | 50 |
| LXXXIII | H | H | —CH₃ | H | H | H | —OCH₂CH₂N(CH₂CH₃)₂ | H | 100 |
| LXXXIV | H | H | —CH₃ | H | H | —Cl | —CH(CH₃)₂ | H | 70 |
| LXXXV | H | H | —CH₃ | H | H | —Cl | —CH₂CH₃ | H | 78 |
| LXXXVI | H | H | —CH₃ | H | H | —Cl | —(CH₂)₃CH₃ | H | 78 |
| LXXXVII | H | H | —CH₃ | H | —OC₄H₉ | H | —COCH₃ | H | 100 |
| LXXXVIII | H | H | —CH₃ | H | H | H | —Cl | —OC₄H₉ | 90 |
| XC | H | H | —CH₃ | H | H | —OC₁₀H₂₁ | —C₁₂H₂₅ | H | 95 |
| XCI | H | H | —CH₃ | H | H | —Cl | —OC₁₀H₂₁ | —Cl | 100 |
| | H | H | —CH₃ | H | H | H | H | H | 100 |
| XCII | H | H | —CH₃ | H | H | H | —N(CH₃)(CH₂C₆H₅) (i.e. —N⟨CH₃, CH₂C₆H₅⟩) | H | 100(a) |
| XCIII | H | H | —CH₃ | H | H | —Cl | —N⟨⟩NCH₂C₆H₅ (piperazinyl) | H | 100(c) |
| XCIV | H | H | —CH₃ | H | H | H | —(CH₂)₃COOH | H | 95 |
| XCV | H | H | —CH₃ | H | H | CH₃ / —OCHC₃H₇ | CH₃ / —OCHC₃H₇ | H | 100(a) |
| XCVI | H | H | —CH₃ | H | H | —Cl | —Cl | H | 100 |
| XCVII | H | H | —CH₃ | H | H | H | —C₄H₉ | H | 100(g) |
| XCVIII | H | H | —CH₃ | H | H | H | —C₄H₉ | H | 100(a) |
| XCIX | H | H | —CH₃ | H | H | —CH₃ | —CH₃ | H | 100(j) |
| C | H | H | —CH₃ | H | H | H | —C₁₀H₂₁ | H | 100(a) |
| CI | H | H | —CH₃ | H | H | H | —C₃H₇ | H | 100(a) |
| CII | H | H | —CH₃ | H | H | H | —C(CH₃)₃ | H | 100(a) |
| CIII | H | H | —CH₃ | H | H | H | —C₆H₁₃ | H | 100(a) |
| CIV | H | H | —CH₃ | H | H | H | —C₅H₁₁ | H | 90(a) |

TABLE I-continued

| EXAMPLE | R² | R³ | R⁷ | R⁸ | A² | A³ | A⁴ | A⁵ | Protection (%) |
|---|---|---|---|---|---|---|---|---|---|
| CV | H | H | —CH₃ | H | H | H | —OC₁₀H₂₁ | H | 100(a) |
| CVI | H | H | —CH₃ | H | H | H | —C₇H₁₅ | H | 100(a) |
| CVII | H | H | —CH₃ | H | H | —F | —F | H | 100(a) |
| CVIII | H | H | —CH₃ | H | H | H | —OC₁₀H₂₁ | H | 100(a)(j) |
| CIX | H | H | —CH₃ | H | H | H | —CN | H | 100 |
| CX | H | H | —CH₃ | H | H | H | —OCH₂-cyclohexyl | H | 100(c) |
| CXI | H | H | —CH₃ | H | H | —Cl | —F | H | 70(c) |
| CXII | H | H | —CH₃ | H | H | —F | H | H | 100(j) |
| CXIII | H | H | —CH₃ | H | —F | H | —F | H | 90(c) |
| CXIV | H | H | —CH₃ | H | —F | H | H | —F | 100(a) |
| CXV | H | H | —CH₃ | H | H | H | —CF₃ | H | 100(a)(j) |
| CXVI | H | H | —CH₃ | H | H | H | —CF₃ | H | 80(c) |
| CXVII | H | H | —CH₃ | H | H | —Cl | N-methylpiperazinyl | H | 100 |
| CXVIII | H | H | —C₆H₅ | H | H | H | —C₄H₉ | H | 80(b)(j) |
| CIX | H | H | —C₆H₅ | H | H | H | morpholino | H | 70(c) |
| CXX | H | H | —C₆H₅ | H | H | H | —OCH₃ | H | 20(c)(j) |
| CXXI | H | H | —C₆H₅ | H | H | —F | —F | H | 96 |
| CXXII | H | H | —C₆H₅ | H | H | H | cyclohexyl | H | 100(c)(h) |
| CXXIII | H | H | —C₆H₅ | H | H | H | —CN | H | 100(c) |
| CXXIV | H | H | H | H | H | H | —C₄H₉ | H | 100(a) |
| CXXV | H | H | H | H | H | —F | —F | H | 100 |
| CXXVI | H | H | H | H | H | H | —CN | H | 80(c)(j) |
| CXXVII | H | H | furyl | H | H | —F | —F | H | 100(c) |

TABLE I-continued

| EXAMPLE | R² | R³ | R⁷ | R⁸ | A² | A³ | A⁴ | A⁵ | Protection (%) |
|---|---|---|---|---|---|---|---|---|---|
| CXXVIII | H | H | (furan-2-yl) | H | H | H | —OCH₃ | H | 100(c) |
| CXXIX | H | —CH₃ | —CH₃ | H | H | H | —C₄H₉ | H | 89(a) |
| CXXX | —C₆H₅ | —CH₃ | —CH₃ | H | H | H | —OCH₃ | H | 100 |
| CXXXI | —C₆H₅ | H | —CH₃ | H | H | H | —OC₄H₉ | H | 100(c) |
| CXXXII | —C₆H₅ | H | —CH₃ | H | H | H | —C₁₂H₂₅ | H | 100(c) |
| CXXXIII | —C₆H₅ | H | —CH₃ | H | H | —OCH₃ | —OCH₃ | H | 100(c) |
| CXXXIV | —C₆H₅ | H | —CH₃ | H | H | H | —OCH₃ | H | 100(c) |
| CXXXV | 2-methoxyphenyl | H | —CH₃ | H | H | H | —OCH₃ | H | 100(a) |
| CXXXVI | —C₆H₅ | H | —CH₃ | H | H | H | —N(CH₃)COCH₃ | H | 100(c) |
| CXXXVII | H | H | —CH₃ | —CH₃ | H | H | —OCH₃ | H | 40(c) |
| CXXXVIII | H | H | —CH₃ | —CH₃ | H | H | —C₄H₉ | H | 100 |
| CXXXIX | —C₆H₅ | H | —CH₃ | H | H | —OCH₃ | —OCH₃ | H | 100(c) |
| CXL | (furan-2-yl) | H | —CH₃ | H | H | —F | —F | H | 100(c) |
| CXLI | (furan-2-yl) | H | —CH₃ | H | H | H | —C₄H₉ | H | 100(c) |
| CXLII | (furan-2-yl) | H | —CH₃ | H | H | H | —OCH₃ | H | 100(e) |

TABLE I-continued

| EXAMPLE | R² | R³ | R⁷ | R⁸ | A² | A³ | A⁴ | A⁵ | Protection (%) |
|---|---|---|---|---|---|---|---|---|---|
| CXLIII | furan-2-yl (O) | H | —CH₃ | H | H | H | —CN | H | 100(c) |
| CXLIV | furan-2-yl (O) | H | —CH₃ | H | H | H | —N(CH₃)COCH₃ | H | 100(f) |
| CXLV | thien-2-yl (S) | H | —CH₃ | H | H | H | —N(CH₃)COCH₃ | H | 100(c) |
| CXLVI | H | H | —CH₃ | —CH₃ | H | —OCH₃ | —OCH₃ | H | 78(c) |
| CXLVII | —CF₃ | H | —CH₃ | H | H | —F | —F | H | 90 |
| CXLVIII | —CF₃ | H | —CH₃ | H | H | H | —C₄H₉ | H | 100(c) |
| CXLIX | H | H | —(CH₂)₄— | | H | H | —OCH₃ | H | 100 |
| CL | H | H | —(CH₂)₄— | | H | H | —C₄H₉ | H | 80 |
| CLI | H | H | —COOC₂H₅ | H | H | H | —OCH₃ | H | 100 |

(a)Quantity of experimental compound administered in each dose was 40 mg/kg.
(b)Quantity of experimental compound administered in each dose was 20 mg/kg.
(c)Quantity of experimental compound administered in each dose was 5 mg/kg.
(d)Quantity of experimental compound administered in each dose was 2 mg/kg.
(e)Quantity of experimental compound administered in each dose was 1 mg/kg.
(f)Quantity of experimental compound administered in each dose was 10 mg/kg.
(g)Experimental compound is 2HCl.
(h)Experimental compound is ½HCl.
(j)Experimental compound is free base.
All structures shown as $C_xH_{2x+1}$ are straight chain alkyl structures. $C_6H_5$ is phenyl.

EXAMPLES CLII-CLXII

Compounds having the following chemical structure were tested for immunomodulating activity using the above test method:

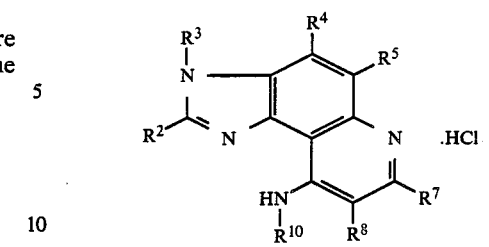
(11)

The results of the tests are provided in Table II:

TABLE II

| EXAMPLE | $R^2$ | $R^3$ | $R^4$ | $R^5$ | $R^7$ | $R^8$ | $R^{10}$ | Protection(%) |
|---|---|---|---|---|---|---|---|---|
| CLII | H | —$CH_3$ | H | H | —$CH_3$ | H | ![4-methoxyphenyl]—⟨⟩—$OCH_3$ | 91 |
| CLIII | H | H | H | H | —$CH_3$ | H | 4-pyridyl | 21 |
| CLIV | H | H | H | H | —$CH_3$ | H | 1-naphthyl | 100 |
| CLV | H | H | H | H | —$CH_3$ | H | 6-(4-methylpiperazinyl)pyridin-2-yl | 100 |
| CLVI | H | H | H | H | —$CH_3$ | H | 6-methoxypyridin-2-yl | 90 |
| CLVII | H | H | H | H | —$CH_3$ | H | 6-piperidinopyridin-2-yl | 100 |
| CLVIII | H | H | H | H | —$CH_3$ | H | $CH_2$—⟨⟩—$OCH_3$ | 100 |
| CLIX | H | H | H | H | —$CH_3$ | H | cyclohexyl | 90 |
| CLX | H | H | H | H | —$CH_3$ | H | $CH_2CH(CH_3)_2$ | 100 |
| CLXI | —$C_6H_5$ | H | H | H | —$CH_3$ | H | —$CH_2$—⟨⟩—$OCH_3$, $OCH_3$ | 100(c) |

TABLE II-continued

| EXAMPLE | R² | R³ | R⁴ | R⁵ | R⁷ | R⁸ | R¹⁰ | Protection(%) |
|---------|----|----|----|----|-----|----|-----|---------------|
| CLXII | H | H | H | H | —CH₃ | H | 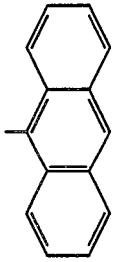 | 0 |

(a) Quantity of experimental compound administered in each dose was 40 mg/kg.
(c) Quantity of experimental compound administered in each dose was 5 mg/kg.
All structures shown as $C_xH_{2x+1}$ are straight chain alkyl structures.
$C_6H_5$ is phenyl.

Another aspect of the present invention is certain imidazo[4,5-f]quinolines which are novel compounds and are useful as immunomodulating agents.

Novel compounds of the present invention include compounds of the class of imidazo[4,5-f]quinolines which conform to the chemical structure of Compounds A except for such imidazo[4,5-f]quinolines which are disclosed in the following references incorporated by reference hereinabove: Spencer and Alaimo U.S. Pat. No. 3,868,378; Spencer and Snyder U.S. Pat. No. 3,878,206; Spencer and Snyder U.S. Pat. No. 3,919,238; Ishiwata and Shiokawa; Spencer, Snyder and Alamio; Spencer, Snyder, Burch and Hatton; Snyder, Spencer and Freedman; and Alaimo, Spencer, Sheffer, Storrin, Hatton and Kohls.

Novel compounds of the present invention include compounds of the class of imidazo[4,5-f]quinolines which conform to the chemical structure of Compounds A, but wherein $R^{10}$ is H, straight or branched chain alkyl, cycloalkyl, aryl, substituted aryl, naphthyl, heteroaryl, substituted heteroaryl, arylalklyl, or substituted arylalkyl; except such compounds wherein $R^{10}$ is phenyl or mono-, di-, or trisubstituted phenyl, $R^2$ is H or methyl or phenyl and $R^3=R^4=R^5=R^8=H$ and $R^7$ is H or methyl or ethyl or phenyl and $R^{10}$ is 2-(4-methyl-1-piperazinyl)-5-pyridyl or 2-methoxy-5-pyridyl or 2-piperidino-5-pyridyl or 4-methoxybenzyl or cyclohexyl or α- or β-naphthyl, or $R^2=R^3=R^4=R^5=R^8=H$ and $R^7$ is methyl and $R^{10}$ is 9-anthryl (Compounds B). Preferred novel compounds of the present invention include Compounds B, wherein $R^7$ is methyl and $R^{10}$ is isobutyl and $R^2=R^3=R^4=R^5=R^8=H$, or $R^2$ is phenyl and $R^7$ is methyl and $R^{10}$ is 3,4-dimethoxyphenylmethyl and $R^3=R^4=R^5=R^8=H$.

Novel compounds of the present invention include compounds of the class of imidazo[4,5-f]quinolines which conform to the chemical structure of Compounds A, but wherein $R^{10}$ is mono-, di- or trisubstituted phenyl; except such compounds wherein $R^2$ is H or methyl or phenyl and $R^3=R^4=R^5=R^8=H$ and $R^7$ is H or methyl or ethyl or phenyl and $R^{10}$ is 4-methylphenyl or 2-chloro-5-methylphenyl or 4-n-butylphenyl or 3-chloro-4-methylphenyl or 4-sec. butylphenyl or 3-trifluoromethylphenyl or 3-trifluoromethyl-4-chlorophenyl or 2-phenylphenyl or 4-phenylphenyl or 2-methyl-3-chlorophenyl or 4-isopropylphenyl or 3,4-dichlorophenyl or 4-bromophenyl or 4-iodophenyl or 4-dimethylaminophenyl or 4-diethylaminophenyl or 3-chloro-4-dimethylaminophenyl or 4-piperidinophenyl or 4-(4-methylpiperazinyl)phenyl or 3-dimethylaminophenyl or 3-chloro-4-piperidinophenyl or 3-chloro-4-(4-methyl)piperazinylphenyl or 3-chloro-4-(4-benzyl)piperazinylphenyl or 4-methoxyphenyl or 4-ethoxyphenyl or 2-methoxyphenyl or 3-chloro-4-ethoxyphenyl or 4-n-butoxyphenyl or 3-methoxyphenyl or 4-phenoxyphenyl or 4-methylthiophenyl or 4-benzyloxyphenyl or 2-methylthiophenyl or 3-methylthiophenyl or 3,4-dimethoxyphenyl or 3,4-diethoxyphenyl or 3,4-diisopropoxyphenyl or 3,4-diisobutoxyphenyl or 3,4-di-n-butoxyphenyl or 3,4-disec. amyloxyphenyl or 2,5-diethoxyphenyl or 2,5-dimethoxyphenyl or 2,5-dimethoxy-4-chlorophenyl or 2-ethoxy-5-methoxyphenyl or 2-methoxy-5-ethoxyphenyl or 2,5-diethoxy-4-chlorophenyl or 2,4-dimethoxy-5-chlorophenyl or 3,4,5-trimethoxyphenyl or 2,4,5-triethoxyphenyl or 4-acetylphenyl or 3-acetylphenyl or 4-n-propionylphenyl or 4-n-butyrylphenyl or 2-methyl-4-chlorophenyl or 3-nitro-4-methylphenyl or 3-chloro-4-ethylphenyl or 3-chloro-4-n-butylphenyl or 3-chloro-4-fluorophenyl or 3-chloro-4-pyrrolidinophenyl or 4-phenylazophenyl or 2-methoxy-4-chlorophenyl or 3,4-methylenedioxyphenyl or 3,4-di-n-amyloxyphenyl or 3,4-diisoamyloxyphenyl or 4-chloro-2,5-di-n-butyoxyphenyl or 4-(2-diethylamino)ethoxyphenyl, or $R^2=R^3=R^4=R^5=R^8=H$ and $R^7$ is methyl and $R^{10}$ is 4-hydroxyphenyl or 3-hydroxyphenyl or 4-acetylaminophenyl or 4-aminophenyl or 4-methylaminophenyl or 4-(1-pyrrolidinyl)phenyl or 4-[N-methyl-N-(2-hydroxyethyl)amino]phenyl or 4-carboxyphenyl or 4-chlorophenyl or 4-fluorophenyl or 4-(N-methylacetylamino)phenyl or 4-benzoylphenyl or 2-methoxy-5-acetylphenyl or 4-(2-hydroxyethyl)phenyl or 3-chlorophenyl or 4-ethylphenyl or 3-chloro-4-hydroxyphenyl or 4-morpholinophenyl or 3-chloro-4-morpholinophenyl or 4-n-dodecylphenyl or 4-carbethoxyphenyl (Compounds C).

Preferred novel compounds of the present invention include Compounds C wherein said substituted phenyls are substituted with groups such as halo, nitro, cyano, hydroxy, $C_1-C_{20}$ straight or branched chain alkyl, cycloalkyl, $C_1-C_{20}$ straight or branched chain alkoxy, aryl, trihalomethyl, aryloxy, arylalkyloxy, cycloalkyloxy, cycloalkylalkyloxy, phenylazo, piperidyl, morpholinyl, pyrrolidyl, alkylpiperazinyl, carboxylic acid and carboxylic acid esters, alkylthio, carboxyalkyl and their esters, hydroxyalkyl, benzoyl, acetyl, propionyl, 2-dialkylaminoethoxy, 3,4-dimethylenedioxy, and/or mono- or disubstituted aminos substituted with H, lower alkyl, hydroxyalkyl and/or alkanoyl. More preferred still are Compounds C wherein said substituted phenyls are substitued with groups such as halo, cyano, $C_1$-$C_{12}$ straight or branched chain alkyl, $C_1$-$C_{10}$ straight or branched chain alkoxy, and/or mono- or disubstituted aminos substituted with H, lower alkyl, hydroxyalkyl, and/or alkanoyl.

More preferred novel compounds of the present invention include Compounds C, wherein $R^7$ is phenyl and $R^{10}$ is 4-(n-morpholino)phenyl and $R^2=R^3=R^4=R^5=R^8=H$, $R^7$ is phenyl and $R^{10}$ is 3,4-difluorophenyl and $R^2=R^3=R^4=R^5=R^8=H$, $R^7$ is phenyl and $R^{10}$ is 4-cyanophenyl and $R^2=R^3=R^4=R^5=R^8=H$, $R^{10}$ is 3,4-difluorophenyl and $R^2=R^3=R^4=R^5=R^7=R^8=H$, $R^{10}$ is 4-cyanophenyl and $R^2=R^3=R^4=R^5=R^7=R^8=H$, $R^7$ is furanyl and $R^{10}$ is 3,4-difluorophenyl and $R^2=R^3=R^4=R^5=R^8=H$, $R^7$ is furanyl and $R^{10}$ is 4-methoxyphenyl and $R^2=R^3=R^4=R^5=R^8=H$. Other preferred novel compounds of the present invention include Compounds C, wherein $R^3$ is methyl and $R^7$ is methyl and $R^{10}$ is 4-n-butylphenyl and $R^2=R^4=R^5=R^8=H$, $R^3$ is methyl and $R^7$ is methyl and $R^{10}$ is 4-methoxyphenyl and $R^2=R^4=R^5=R^8=H$, $R^2$ is phenyl and $R^7$ is methyl and $R^{10}$ is 4-n-dodecylphenyl and $R^3=R^4=R^5=R^8=H$, $R^2$ is phenyl and $R^7$ is methyl and $R^{10}$ is 4-cycloamyloxyphenyl and $R^3=R^4=R^5=R^8=H$, $R^2$ is 2-methoxyphenyl and $R^7$ is methyl and $R^{10}$ is 4-methoxyphenyl and $R^3=R^4=R^5=R^8=H$, $R^2$ is phenyl and $R^7$ is methyl and $R^{10}$ is 4-(N-methylactylamino)phenyl and $R^3=R^4=R^5=R^8=H$, $R^7$ is methyl and $R^8$ is methyl and $R^{10}$ is 4-methoxyphenyl and $R^2=R^3=R^4=R^5=H$, or $R^7$ is methyl and $R^8$ is methyl and $R^{10}$ is 4-n-butylphenyl and $R^2=R^3=R^4=R^5=H$. Other preferred novel compounds of the present invention include Compounds C, wherein $R^2$ is furanyl and $R^7$ is methyl and $R^{10}$ is 3,4-dimethoxyphenyl or 3,4-difluorophenyl or 4-n-butylphenyl or 4-methoxyphenyl or 4-cyanophenyl or 4-(N-methylacetylamino)phenyl and $R^3=R^4=R^5=R^8=H$. Other preferred novel compounds of the present invention include Compounds C, wherein $R^2$ is 2-thienyl and $R^7$ is methyl and $R^{10}$ is 4-acetylaminophenyl and $R^3=R^4=R^5=R^8=H$, $R^7$ is methyl and $R^8$ is methyl and $R^{10}$ is 3,4-dimethoxyphenyl and $R^2=R^3=R^4=R^5=H$, $R^2$ is trifluoromethyl and $R^7$ is methyl and $R^{10}$ is 3,4-difluorophenyl and $R^3=R^4=R^5=R^8=H$, $R^2$ is trifluoromethyl and $R^7$ is methyl and $R^{10}$ is 4-n-butylphenyl and $R^3=R^4=R^5=R^8=H$, $R^7$ and $R^8$ are connected by n-butylene and $R^{10}$ is 4-methoxyphenyl and $R^2=R^3=R^4=R^5=H$, $R^7$ and $R^8$ are connected by n-butylene and $R^{10}$ is n-butylphenyl and $R^2=R^3=R^4=R^5=H$, or $R^7$ is propionyl and $R^{10}$ is 4-methoxyphenyl and $R^2=R^3=R^4=R^5=R^8=H$. Other preferred novel compounds of the present invention include Compounds C, wherein $R^2=R^3=R^4=R^5=R^8=H$ and $R^7$ is methyl and $R^{10}$ is 3,4-di-n-dodceylphenyl or 2,4-dichlorophenyl or 4-carboxy-n-propylphenyl or 3,4,5-trichlorophenyl or 3,4-dimethylphenyl or 4-n-decylphenyl or 4-n-propylphenyl or 4-isobutylphenyl or 4-n-hexylphenyl or 4-n-amylphenyl or 4-n-decyloxyphenyl or 4-n-septylphenyl or 3,4-difluorphenyl or 4-cyanophenyl or 4-cyclohexylmethoxyphenyl or 3-fluorophenyl or 2,4-difluorophenyl or 2,5-difluorophenyl or 4-trifluoromethylphenyl or 3,5-dichloro-4-methylpiperazinophenyl.

Especially preferred novel compounds of the present invention include compounds 3, 4, 5, 6 and 7 hereinabove.

IMIDAZO[4,5-f]QUINOLINE PREPARATION

The imidazo[4,5-f]quinolines useful in the immune system enhancing method of the present invention can be prepared in the general manner described in a number of the articles and patents hereinbefore incorporated by reference. For example, Alaimo, Spencer, Scheffer, Storrin, Hatton and Kohls, *Journal of Medicinal Chemistry*, 21 (3), pp. 298–300 (1978), referenced hereinbefore, disclose that a series of 2-arylimidazo[4,5-f]quinolin-9-ols have been prepared by a multistep procedure from various 5-amino-benzimidazoles. Such a procedure is illustrated in Scheme I:

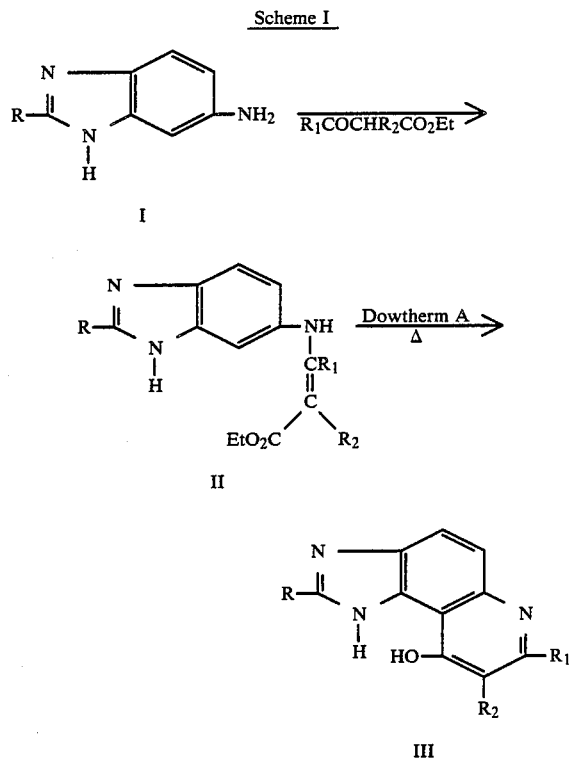

As shown in Scheme I, the imidazo[4,5-f]quinolin-9-ols III were prepared by the condensation of a 5-amino-2-substituted benzimidazole I with the appropriate β-keto ester, followed by thermal cyclization of the resultant benzimidazolylacrylate II in boiling Dowtherm A.

An example of imidazo[4,5-f]quinolinol synthesis of this type is provided in this journal article as follows:

PREPARATION EXAMPLE I 2-(2-Furyl)-7-methyl-1H-imidazo[4,5-f]quinolin-9-ol Tetartohydrate

A. 2-(2-Furyl)-5-nitrobenzimidazole

A mixture of 1,2-diamino-4-nitrobenzene (31 g, 0.2 mol) and 2-furancarboxaldehyde (25 g, 0.26 mol) in 2-propanol is treated with p-benzoquinone (24 g, 0.22 mol). The reaction mixture is heated under reflux for 2 h. The reaction solution is diluted with water to precipitate the product. After drying, the crude product weighs 46 g (100%). Recrystllization from nitromethane provides an analytical sample which melts at 228°–229° C. Anal. Calcd for $C_{11}H_7N_3O_3$; C, 57.64; H, 3.08; N, 18.34. Found: C, 57.55; H, 3.04; N, 18.53.

B. 3-[[2-(2-Furyl)-2-benzimidazolyl]amino]crotonate

A solution of 2-(2-furyl)-5-nitrobenzimidazole (66 g, 0.29 mol) in 2-propanol (500 mL) is subjected to catalytic hydrogenation at 40 psi of initial pressure over Raney nickel catalyst. After the hydrogen uptake is complete, the catalyst is removed and the filtrate refluxed for 8 h with ethyl acetoacetate (38 g, 0.29 mol), anhydrous CaSO$_4$ (100 g), and HOAc (20 mL). The CaSO$_4$ is removed and the filtrate concentrated in vacuo to give 66 g (74%) of product. Recrystallization from nitromethane gives analytical material which melts at 177°-178° C. Anal. Calcd for C$_{17}$H$_{17}$N$_3$O$_3$: C, 65.58; H, 5.50; N, 13.50. Found: C, 65.48; H, 5.47; N, 13.47.

C. 2-(2-Furyl)-7-methyl-1H-imidazo[4,5-f]quinolin-9-ol

Dowtherm A (500 mL) is preheated to 230° C. and to it is added 3-[[2-(2-furyl)-5-benzimidazolyl]amino]crotonate (38.5 g, 0.1 mol) in small portions. After the addition is complete, the reaction mixture is maintained at 230° C. for 15 min and then poured into a beaker and allowed to cool.

The precipitated product is filtered and washed thoroughly with hexane to give 20 g (74%). Recrystallization from nitromethane gives analytical material which melts at 280°-282° C. Anal. Calcd for C$_{15}$H$_{11}$N$_3$O$_2$.0.25-H$_2$O: C, 66.78; H, 4.30; N. 15.58. Found: C, 66.56; H, 4.43; N, 15.40.

Imidazo[4,5-f]quinolinol syntheses of the Scheme I type can also be found in the hereinbefore referenced U.S. Pat. No. 3,868,378. Representative examples from this patent are set forth as follows in Preparation Examples II–IV:

PREPARATION EXAMPLE II 2-(2-Furyl)-7-methyl-1H-imidazo[4,5-f]quinolin-9-ol Tetartohydrate

A. N-(2-Amino-4-nitrophenyl)-2-furamide

To a stirred solution of 4-nitro-o-phenylene diamine (76.5 g, 0.5 mole) in 500 ml of pyridine, is added dropwise 2-furoyl chloride (65 g, 0.5 mole). After the addition is complete the reaction solution is stirred at room temperature for 15 minutes and then at reflux for 2 hr. The hot reaction solution is poured into 6 liters of water to give an oil, which solidifies upon standing overnight at room temperature to give 125 g (100 percent) of yellow intermediate. The solid is used in part B without further purification.

B. 2-(2-Furyl)-5-nitro-benzimidazole

A stirred mixture of N-(2-amino-4-nitrophenyl)-2-furamide (125 g, 0.5 mole) in a solution of concentrated hydrochloric acid (400 m) and 850 ml of water is heated on a steam bath for 3 hr. The reaction mixture after pouring into 4 liters of ice is treated with concentrated ammonium hyroxide until basic. The intermediate is filtered to give 104 g (91 percent).

C. 5-Amino-2-(2-furyl)benzimidazole

A solution of 2-(2-furyl)-5-nitrobenzimidazole (52 g, 0.2 mole) in 1 liter of absolute ethyl alcohol is reduced (Parr apparatus) using 5 percent palladium on carbon (50 percent wet) catalyst. An uptake of 44 lbs. (100 percent of theory) of hydrogen in one-half hr is noted. After the reduction is complete the catalyst is removed by filtration. The filtrate is used in part D.

D. Ethyl 3-[2-(2-Furyl)-5-benzimidazolylamino]crotonate

A stirred mixture of the filtrate from part C (0.45 mole), 100 g of anhydrous calcium sulfate, ethyl acetoacetate (58.5 g, 0.45 mole), and 3 ml of glacial acetic acid, is heated at reflux for 12 hours. The warm reaction mixture is filtered. The filtrate is stripped in vacuo to give an oil which is triturated with anhydrous ether to give, after filtration, 77 g of tan solid (55 percent).

E. 2-(2-Furyl)-7-methyl-1H-imidazo[4,5-f]quinolin-9-ol Tetartohydrate

To a preheated (230°) solution of Dowtherm (500 ml) is added portion-wise 3-[[2-(2-furyl)-5-benzimidazolyl]amino]crotonate (38.5 g, 0.1 mole). After the addition is complete the reaction mixture is kept at 230° for 15 minutes, then decanted into a beaker to form, upon cooling, a tan precipitate. The precipitate is filtered and washed with hexane to give 20 g (74 percent) of tan solid. Recrystallization from CH$_3$NO$_2$ gives m.p. 280°-282°. Anal. Calcd. for C$_{15}$H$_{11}$N$_3$O$_2$-¼H$_2$O: C, 66.78; H, 4.30; N, 15.58. Found: C, 66.56; H, 4.43; N, 15.40.

PREPARATION EXAMPLE III 8,9-Dihydro-2-phenyl-7H-cyclopenta[2,3]-1H-imidazo[4,5-f]quinolin-10-ol

A. Ethyl 2-[2-phenyl-5-benzimidazolyl)amino]-1-cyclopentene carboxylate

A mixture of 64 g (0.41 moles) of ethyl 2-cyclopentanonecarboxylate, 86 g (0.41 moles) of 2-phenyl-5-aminobenzimidazole, 100 g of anhydrous calcium sulfate, 0.5 ml of HOAc and 1000 ml of ethanol is refluxed overnight with stirring. The calcium sulfate is removed by filtration and the ethanol filtrate concentrated to dryness in vacuo to yield 179 g of brown oil which solidifies upon standing.

B. 8,9-Dihydro-2-phenyl-7H-cyclopenta[2,3]-1H-imidazo[4,5-f]quinolin-10-ol

To 1,700 ml of boiling Dowtherm is added 179 g (0.52 moles) of ethyl 2-[2-phenyl-5-benzimidazolyl)amino]-1-cyclopentane carboxylate (part A). The reaction mixture is heated at reflux for 30 min then allowed to cool to room temperature. The brown solid is collected by filtration, washed with Dowtherm, acetone and ether and then air-dried to give 127 g, m.p. 350°-393° C. The crude product is recrystallized from 500 ml of dimethylformamide with charcoal to give 60 g, m.p. 369°-375° C. Anal. Calcd for C$_{19}$H-N$_3$O: C, 75.23; H, 5.02; N, 13.95. Found: C, 75.27; H, 5.06; N, 13.84.

PREPARATION EXAMPLE IV 7,8-Dimethyl-2-phenyl-1H-imidazo[4,5-f]quinolin-9-ol Hemihydrate

A. Ethyl 3-[5-(2-phenylbenzimidazolyl)amino]-2-methyl crotonate

A mixture of 90 g (0.43 moles) of 2-phenyl-5-aminobenzimidazole, 62 g (0.43 moles) of ethyl 2-methylacetoacetate, 100 g of anhydrous calcium sulfate, 0.5 ml of HOAc and 1,000 ml of ethanol is heated under reflux overnight. The anhydrous calcium sulfate is filtered off and the ethanol filtrate concentrated in vacuo to give 143 g of brown oil.

B.
7,8-Dimethyl-2-phenyl-1H-imidazo[4,5-f]quinolin-9-ol Hemihydrate

To 1,500 ml of boiling Dowtherm is added 143 g (0.43 moles) of ethyl 3-[5-(2-phenylbenzimidazolyl)amino]-2-methyl crotonate (part A). The reaction mixture is heated at reflux for 30 min, then allowed to cool to room temperature. The crude product is collected by filtration, washed with Dowtherm, acetone, ether and oven dried (100° C.) to give 86 g, m.p. 328°-338° C. Recrystallization from 1,000 ml of dimethylformamide H$_2$O, with charcoal, yields 63 g. Anal. Calcd for C$_{18}$H$_{15}$N$_3$O.½H$_2$O: C, 72.46; H, 5.41; N, 14.09; Found: C, 72.85; H, 5.36; N, 14.13.

Additional examples of imidazo[4,5-f]quinolinol synthesis also of this type are disclosed in the processes utilized in the hereinbefore referenced U.S. Pat. No. 3,919,238 to prepare 9-(substituted amino)imidazo[4,5-f]quinolines. These examples are set forth as follows:

PREPARATION EXAMPLE V

7-Methyl-2-phenyl-9-imidazo[4,5-f]quinolinol

A. 2,4-Dinitrophenylbenzamide

To a solution of 73.2 g. (0.4 m.) of 2,4-dinitroaniline in 400 ml. of pyridine with stirring and slight warming is added 56.2 g. (0.4 m.) of benzoyl chloride in about 10 min.; the temperature rises from 40° to 50°. Then the dark solution is heated at reflux for 2½ hours. After standing overnight, the yellow solid is collected, washed with H$_2$O until no pyridine odor is detectable. This 90 g. of crude product is recrystallized from about 2.1 of CH$_3$CN to yield 44 g. (38%) of yellow product melting at 201°-205°.

B. 2-Phenyl-5-aminobenzimidazole

A mixture of 44 g. (0.153 m.) of 2,4-dinitrophenylbenzamide in 800 ml. of ethanol together with 6 g. of 5% Pd/C containing 50% H$_2$O is subjected to reduction. Absorption stops after 60.5 lb. of uptake of hydrogen (theory=61.5 lb.) in 2½ hour. The reduction mixture is warmed on steam bath with the addition of about 2½ 1 ethanol. The mixture is then filtered hot and crystalline needles separate from the filtrate. This product is collected, washed with ethanol, ether and airdired; m.p. 218°-220°. Concentration of the filtrate yields more solid. The solids are combined and suspended in 250 ml. of H$_2$O with the addition of 25 ml. of conc. HCl. The mixture is then heated on the steam bath for 1½ hours. After cooling, the reaction mixture is diluted with H$_2$O to give a dark solution which, upon neutralization with conc. NH$_4$OH, yields 30 g. (94%) of tan solid after washing with H$_2$O and drying at 100°. It decomposes at 235°-250°.

C. Ethyl 3-[5-(2-phenylbenzamidazoylamino)]crotonate

A mixture of 275 g. (1.32 m.) of 2-phenyl-5-aminobenzimdiazole, 171 g. (1.32 m.) of ethyl acetoacetate, 200 g. of anhydrous calcium sulfate, 13 ml. of glacial HOAc and 3000 ml. of ethanol is refluxed overnight. After filtration the solution is concentrated in vacuo until a solid remains. Another run is made in the same manner and the products combined to give a total yield of 861 g.

D. 7-Methyl-2-phenyl-9-imidazo[4,5-f]quinolinol.

To 8000 ml. of boiling Dowtherm ® is added 430 g. (1.34 m.) of ethyl 3-[5-(2-phenylbenzimidazoylamino)]-crotonate. The reaction is heated at reflux for 90 min. then allowed to cool to room temperature. The crystalline solid is triturated in acetone, filtered and air-dried to give 745 g. m.p. 147°-172°. The crude product is recrystallized from 3000 ml. of dimethylformamide. The yield after oven-drying (100°) is 69 g., m.p. 332°-335° with decomposition. By diluting the dimethylformamide filtrate with H$_2$O, another 188 g. is obtained, m.p. 197°-230° with decomposition, which is recrystallized from 700 ml. of dimethylformamide to yield 50 g. m.p. 332°-336° with decomposition.

Anal. Calcd. for C$_{17}$H$_{13}$N$_3$O: C, 74.16; H, 4.76; N, 15.27. Found: C, 73.79; H, 4.68; N, 15.27.

Spencer, Snyder and Alaimo, *Journal of Heterocyclic Chemistry*, 12 (6), pp. 1319–1321 (1975), incorporated by reference hereinbefore, disclose 9-chloro-(or hydroxy)-2 and/or 7-substituted-imidazo[4,5-f]quinolines. These compounds were synthesized by the reaction sequence shown in Scheme II:

Scheme II

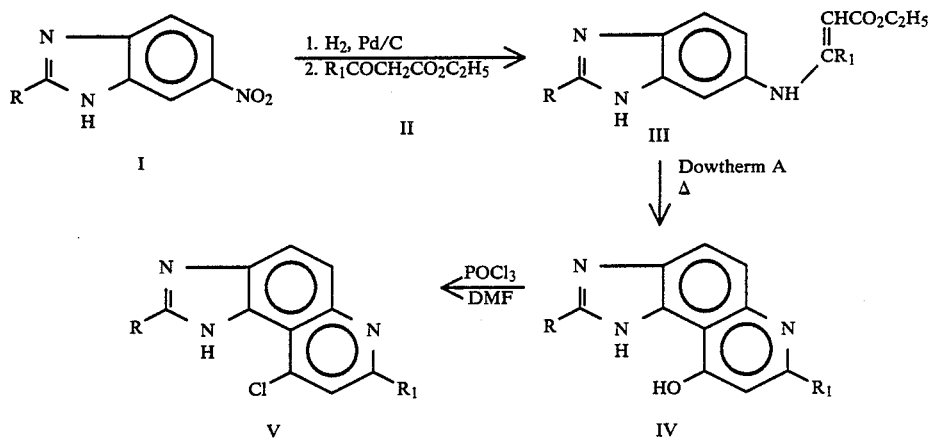

The Scheme II procedure is similar to that reported by Ishiwata and Shiokawa (*Chemical Pharmaceutical Bulletin*, 17, pp. 2455–2460 (1969); incorporated by reference hereinbefore) with two variations: the sequence started with 5-nitrobenzimidazoles I, and the intermediate 9-hydroxyimidazo[4,5-f]quinolines IV were isolated and characterized. The starting nitrobenzimidazoles I were reduced catalytically and the resulting aminobenzimidazoles, which were not isolated, were condensed with the appropriate β-ketoesters II to yield the crotonates, or cinnamates, III. Using boiling Dowtherm A, the esters III were cyclized to the corresponding 9-hydroxyimidazo[4,5-f]quinolines IV. The hydroxy compounds IV were converted smoothly to the 9-chloroimidazo[4,5-f]quinolines V with phosphorus oxychloride using DMF as a solvent.

The Spencer et al., *Journal of Heterocyclic Chemistry*, 12(6) article also discloses the preparation of 9-hydroxyimidazo[4,5-]quinoline achieved by the sequence shown in Scheme III:

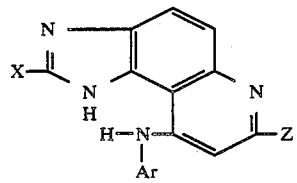

As shown in Scheme IV, these compounds were prepared by treating the appropriate 9-chloroimidazo[4,5-f]quinoline (I) with the prerequisite amine in refluxing EtOH or DMF. The intermediates I were prepared by

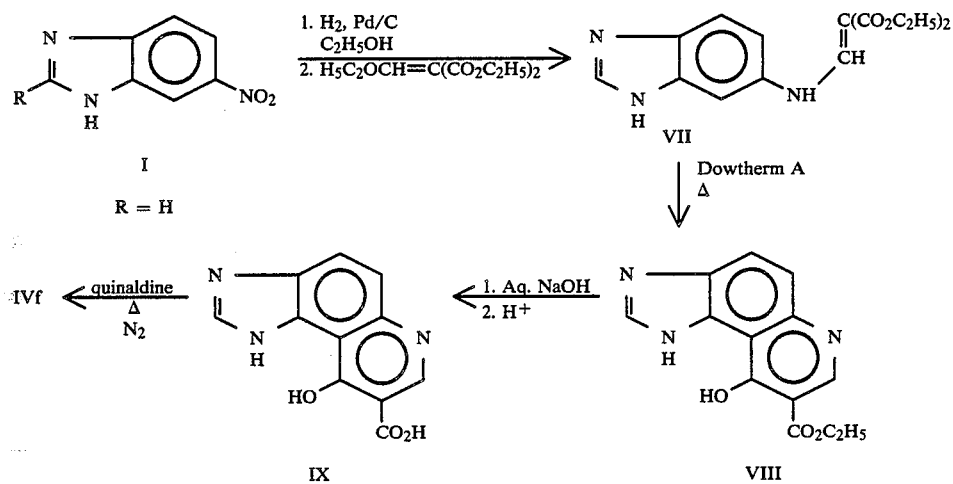

As shown in Scheme III, catalytic redution of 5-nitrobenzimidazole (I, R=R₁=H) yielded 5-aminobenzimidazole which, without isolation, was condensed with diethyl ethoxymethylenemalonate (VI) to give diethyl (5-benzimidazolyl)aminomethylenemalonate (VII). Compound VII was cyclized thermally in boiling Dowtherm A to yield ethyl 9-hydroxy-1H-imidazo[4,5-f]quinoline-6-carboxylate (VIII). Hydrolysis of VIII gave the free acid IX which was converted to 9-hydroxyimidazo[4,5-f]quinoline (IVf) by decarboxylation in boiling quinaldine.

Spencer, Snyder, Burch and Hatton, *Journal of Medicinal Chemistry*, 20(6), pp. 829-833 (1977), incorporated by reference hereinbefore, disclose that a number of 9-(substituted amino)imidazo[4,5-f]quinolines have been prepared from the above described 9-chloroimidazo[4,5-f]quinolines. Such a reaction is shown in Scheme IV.

the method of Spencer et al. (*Journal of Heterocyclic Chemistry*, 12(6), pp. 1319-1321 (1975); incorporated by reference hereinbefore).

The hereinbefore referenced U.S. Pat. Nos. 3,919,238 and 3,878,206 set forth a number of examples of synthesis of 9-(substituted amino)imidazo[4,5-f]quinoline compounds which can be employed in the method of the present invention. Four representative examples, from U.S. Pat. No. 3,919,238, are set forth as follows:

PREPARATION EXAMPLE VI 9-(p-Anisidino)-7-phenyl-1H-imidazo[4,5-f]quinoline Hydrochloride A. Ethyl 3-(5-Benzimidazolylamino)cinnamate A solution of 900 ml. of ethanol and 82 g. (0.5 mole) of 5-nitrobenzimidazole with 4 g. of 5% PdC, 50% H₂O catalyst is reduced on the Parr Apparatus. A pressure drop of 104 psi. is observed (calcd. 100). After the reduction stopped, the bottle is removed from the apparatus, and the catalyst filtered. Then 96 g. (0.5 mole) of ethylbenzoylacetate, 20 g. of anhydrous calcium sulfate and 0.5 ml. of HOAc are added to the filtrate. The solution is refluxed for 2 hours and filtered. The filtrate is concentrated to a dark sticky resin. Crystallization is induced by scratching. The product after cooling is filtered, washed with ethanol and air-dried. The product weighs 55 g. m.p. 188°-190° C.

B. 7-Phenyl-1H-imidazo[4,5-f]quinolin-9-ol

Into a 1000 ml. three-necked flask equipped with a thermometer and heated with a mantle, 300 ml. of Dowtherm is heated to boiling, then 30 g. of A. is added. The solution is boiled for 10 mintues. The flask is removed from the mantle and allowed to cool. The product is filtered and washed with fresh Dowtherm, then acetone, and air-dried. The product weighs 10 g. m.p.>300° C. Four more runs are made. All five runs combine into one large sample containing 58 g. This sample is recrystallized from dimethylformamide. The product weighs 43 g. m.p. 318°–320° C.

C. 9-Chloro-7-phenylimidazo[4,5-f]quinoline

To a mixture of 121 g. (0.46 m.) of B. and 424 ml. (712 g. 4.6 m.) of $POCl_3$ is added dropwise over 3 hr., 848 ml. of dimethylformamide. The yellow mixture is allowed to stir overnight then poured into 5 liters of ice. The yellow precipitate is collected by filtration, washed with cold $H_2O$ and air-dried to give 161 g. Following a trituration in 500 ml. of 2N NaOH solution, the product is filtered, washed with $H_2O$ and oven-dried (100° C.) to yield 118 g. m.p. 229°–400° C., slow decomposition.

Anal. Calcd. for $C_{16}H_{10}ClN_3$: C, 68.70; H, 3.60; N, 15.02; Cl, 12.68. Found: C, 69.04; H, 3.63; N, 15.07; Cl, 12.59.

D. 9-(p-Anisidino)-7-phenyl-1H-imidazo[4,5-f]quinoline Hydrochloride

A mixture of 27.98 g. (0.1 m.) of C., 12.3 g. (0.1 m.) of p-anisidine and 200 ml. of dimethylformamide is refluxed with stirring overnight. The reaction mixture is chilled, filtered and air-dried to give 49 g. The crude product is recrystallized from 1000 ml. of ethanol, with charcoal, then concentrated to one-half its volume and chilled. A second recrystallization from 250 ml. of dimethylformamide yields 19 g. It is then stirred in hot water, filtered and oven-dried (100° C.) to give 17 g. Anal. Calcd. for $C_{23}H_{18}N_4O \cdot HCl$: C, 68.57; H, 4.75; N, 13.91; Cl, 8.60. Found: C, 68.81; H, 4.72; N, 13.97; Cl, 7.24.

PREPARATION EXAMPLE VII

9-(p-Anisidino)-1H-imidazo[4,5-f]quinoline Hydrochloride Tetartohydrate

A. Ethyl 9-Hydroxy-1H-imidazo[4,5-f]quinoline-9-carboxylate

An 82 g. portion (0.5 mole) of 5-nitrobenzimidazole in 1 L of ethanol is reduced over 5 g. of 5% palladium-charcoal catalyst containing 50% water. The reduction stops after a pressure drop of 97 psig. (97%) in 75 min. The catalyst is filtered, 108 g. (0.5 mole) of diethoxymethylenemalonate is added to the filtrate and the solution is boiled in an open flask until about one-half of the solvent has boiled away (ca. 2 hr.). The product sets to a solid cake upon cooling. Ethanol containing a little water is added to assist in breaking up the cake and the product is filtered, washed with cold ethanol-$H_2O$ (3:1) and air-dried; yield, 125 g. (83%). A 50 g. portion of this anil is added to 500 ml. of boiling Dowtherm over a 3–4 min. period and boiling is continued 4 min. longer. After cooling to room temperature the product is filtered, washed with Dowtherm, then benzene and air-dried; 44 g. of crude product is obtained. Extraction of this material with 500 ml. of boiling ethanol gives 22 g., m.p. 315°–316° C.

B. 9-Hydroxyimidazo[4,5-f]quinoline-8-carboxylic Acid

A mixture of 356 g. (1.384 mole) of A. and 3000 ml. of 2N NaOH solution is heated at reflux for 3 hours. The solution is stirred for 1 hour with charcoal, filtered, and acidified with 509 ml. of concentrated HCl. The crude product is collected by filtration, washed with $H_2O$, then acetone, and air-dried to give 380 g. m.p. 304°–308°.

After dissolving 40 g. of the crude product in 3000 ml. of dimethylformamide, with charcoal, the filtrate is diluted with 3000 ml. of $H_2O$. It is then filtered, washed with acetone and oven-dried (100°) to give 35.5 g. A second recrystallization from 3000 ml. of dimethylformamide, with charcoal and concentration of the filtrate to a volume of 500 ml. yields 29 g. m.p. 358°–360°.

Anal. Calcd. for $C_{11}H_7N_3O_3$: C, 57.64; H, 3.08; N, 18.34. Found: C, 57,65; H, 3.05; N, 18.12.

C. 9-Imidazo[4,5-f]quinolinol

A mixture of 254 g. (1.108 mole) of B. and 1400 ml. of quinaldine is heated at reflux for 9 hours while passing nitrogen into the mixture. The brown solid is collected by filtration, washed with benzene and air-dried to give 183 g. It is then suspended in 3000 ml. of $H_2O$, and 150 ml. of conc. HCl added to pH 2.5. After stirring for 60 min. the solution is filtered. The filtrate is chilled to 20° C., and conc. $NH_4OH$ added to a pH 8-pH 9. The brown precipitate is collected by filtration, washed with $H_2O$ and oven-dried (100° C.) to yield 182 g. m.p. 366°–368° C.

Anal. Calcd. for $C_{10}H_7N_3O$: C, 64.86; H, 3.81; N, 22.69. Found: C, 64.88; H, 3.82; N, 22.69.

D. 9-Chloroimidazo[4,5-f]quinoline

To a mixture of 150 g. (0.813 mole) of C. and 743 ml. (1244 g. 8.13 mole) of $POCl_3$ is added dropwise over 5 hours, 1486 ml. of dimethylformamide. The brown mixture is allowed to stir overnight at room temperature then slowly poured into 5 liters of ice. The solution is basified to pH 8 using 2800 ml. of conc. $NH_4OH$. It is then filtered, washed with water and air-dried to give 304 g. The crude product is dissolved in 16 liters of MeOH filtered hot to remove the insolubles, and the MeOH filtrate concentrated in vacuo to give 141 g. A second recrystallization from 4000 ml. of MeOH, with charcoal, yields 82.5 g.

Anal. Calcd. for $C_{10}H_5ClN_3$: C, 59.27; H, 2.49; N, 20.74; Cl, 17.50. Found: C, 58.99; H, 2.99; N, 20.69; Cl, 17.09.

E. 9-(p-Anisidino)-1H-imidazo[4,5-f]quinoline Hydrochloride Tetartohydrate

A mixture of 20.3 g. (0.1 mole) of D., 12.3 g. (0.1 mole) of panisidine and 250 ml. of ethanol is refluxed with stirring for 10 hours. The reaction solution is chilled and the solid collected by filtration, washed with ether and air-dried. The crude product is recrystallized from 4000 ml. of ethanol with charcoal to yield 19 g.

Anal. Calcd. for $C_{17}H_{14}N_4O \cdot HCl \cdot \frac{1}{4}H_2O$: C, 61.63; H, 4.72; N, 16.91; Cl, 10.70. Found: C, 61.38; H, 5.08; N. 16.91; Cl, 10.91.

PREPARATION EXAMPLE VIII 9-(p-Anisidino)-7-methyl-2-phenyl-1H-imidazo[4,5-f]quinoline Hydrochloride Hemihydrate

A. 9-Chloro-7-methyl-2-phenylimidazo[4,5-f]quinoline

To a mixture of 88 g. (0.32 m.) of 7-methyl-2-phenyl-9-imidazo[4,5-f]quinolinol (Example V D above) and 293 ml. (481 g. 3.2 m.) of $POCl_3$ is added slowly 586 ml. of dimethylformamide. Following the completion of the addition, stirring is continued overnight at room temperature. It is then poured into 4 liters of ice. The crude product is precipitated by the addition of 1200 ml. of conc. $NH_4OH$ to pH 8.0. It is collected by filtration, washed with $H_2O$ and air-dried to give 154 g. m.p. 136°–250° C., slow decomposition. After dissolving the crude product in 5 liters of MeOH, the MeOH filtrate is concentrated to a volume of 750 ml. and chilled. The yield after oven-drying (100° C.) is 41 g. A second recrystallization from 2000 ml. of MeOH and followed by concentration to one-half its volume yields 28 g.

Anal. Calcd. for $C_{17}H_{12}ClN_3$: C, 69.51: H, 4.12; N, 14.31; Cl, 12.07. Found: C, 69.38; H, 4.27; N, 14.32; Cl, 12.22.

B. 9-(p-Anisidino)-7-methyl-2-phenyl-1H-imidazo[4,5-f]quinoline Hydrochloride Hemihydrate A mixture of 17.5 g. (0.06 m.) of A., 7.4 g. (0.06 m.) of p-anisidine and 250 ml. of dimethylformamide is refluxed with stirring overnight. The reaction mixture is chilled, filtered, washed with ether and air-dried to give 23 g. m.p. 215°–315° C. The crude product is recrystallized from 1000 ml. of ethanol to yield 17 g.

Anal. Calcd. for $C_{24}H_{20}N_4O.HCl.\frac{1}{2}H_2O$: C, 67.58; H, 5.21; N, 13.16; Cl, 8.33. Found: C, 67.40; H, 5.53; N, 13.21; Cl, 8.00.

PREPARATION EXAMPLE IX 9-(p-Anisidino)-2,7-dimethyl-1H-imidazo[4,5-f]quinoline Hydrochloride

A. Ethyl 3-[5-(2-Methylbenzimidazolyl)amino]crotonate

To a mixture of 90 g. (0.49 m.) of 5-amino-2-methylbenzimidazole hydrochloride in 1500 ml. of MeOH and 50 ml. of $H_2O$ is added portionwise 150 g. of $NaHCO_3$. The mixture is refluxed for 60 minutes, then cooled and filtered. The filtrate is heated on a steam bath until the MeOH had boiled off then cooled and filtered to remove the solid (mostly NaCl). After the addition of ethanol to the filtrate, the mixture is again heated on a steam bath to a low volume, cooled and filtered. The filtrate is concentrated in vacuo to give a dark, glassy solid. After adding 300 ml. of benzene, 200 ml. of ethanol, 65 g. (0.5 m.) of ethyl acetoacetate and a quantity of anhydrous calcium sulfate, the mixture is refluxed 3 hours. It is then filtered hot and concentrated in vacuo to a dark gummy residue. The crude product is dissolved in 200 ml. of ethanol and precipitated with 300 ml. of $H_2O$ to yield 54 g., m.p. 140°–144° C. of white needles.

B. 2,7-Dimethyl-1H-imidazo[4,5-f]quinolin-9-ol

To 1500 ml. of boiling Dowtherm is added portionwise 105 g. (0.406 m.) of ethyl 3-[5-(2-methylbenzimidazolyl)amino]crotonate. The reaction mixture is heated at reflux for 30 minutes, then allowed to cool to room temperature. The brown solid is collected by filtration, washed with Dowtherm, acetone and then air-dried to give 70 g, m.p.>400° C. The crude product is recrystallized from 2500 ml. of dimethylformamide to yield 37.5 g. m.p.>400° C.

C. 9-Chloro-2,7-dimethylimidazo[4,5-f]quinoline

To a mixture of 31 g. (0.146 m.) of 2,7-dimethyl-1H-imidazo[4,5-f]quinoline-9-ol and 1336 ml. (223 g. 1455 m.) of $POCl_3$ is added dropwise 267.2 ml. of dimethylformamide. The mixture is stirred overnight at room temperature, then poured into 1000 ml. of ice. The solution is basified to pH 8.0 using conc. $NH_4OH$, keeping the temperature below 20° C. It is then filtered, washed with $H_2O$ and air-dried. The crude product is recrystallized from 2000 ml. of MeOH, and concentrated in vacuo to yield 338 g. m.p. 314°–330° C.

D. 9-(p-Anisidino)-2,7-dimethyl-1H-imidazo[4,5-f]quinoline Hydrochloride

A mixture of 18.5 g. (0.08 m.) of 9-chloro-2,7-dimethylimidazo[4,5-f]-quinoline, 9.85 g. (0.08 m.) of p-anisidine and 300 ml. of ethanol is refluxed, with stirring, overnight. The solution is concentrated in vacuo to give 27 g. m.p. 307°–311° C. Recrystallization from 300 ml. of MeOH yields 13 g. m.p. 317°–318° C.

Anal. Calcd. for $C_{19}H_{18}N_4O.HCl$: C, 64.31; H, 5.40; N, 15.79; Cl, 9.99. Found: C, 64.46; H, 5.47; N, 15.77; Cl, 9.92.

The novel 9-(substituted amino)imidazo[4,5-f]quinoline compounds of the present invention can be prepared by one of ordinary skill in the art utilizing the general synthesis methods described above. Such methods can be carried out in a manner similar to that set forth in Preparation Examples I–IX using appropriately substituted commercially-available or easily synthesized starting materials.

Another aspect of the present invention is a composition in dosage unit form for enhancing the immune response system of mammals comprising an effective but nontoxic amount of the novel imidazo[4,5-f]quinolines having immunomodulating activity disclosed hereinabove. The composition is preferably adapted to systemic administration to mammals.

As used herein, the term "pharmaceutical carrier" denotes a solid or liquid filler, diluent, or encapsulating substance. Some examples of the substances which can serve as pharmaceutical carriers are sugars, such as lactose, glucose, and sucrose; starches, such as corn starch and potato starch; cellulose and its derivatives, such as sodium carboxymethylcellulose, ethylcellulose, and cellulose acetate; powdered tragacanth; malt; gelatin; talc; stearic acid; magnesium stearate; calcium sulfate; vegetable oils, such as peanut oil, cottonseed oil, sesame oil, olive oil, corn oil, and oil of theobroma; polyols, such as propylene glycol, glycerin, sorbitol, manitol, and polyethyleneglycol; agar; alginic acid; pyrogen-free water; isotonic salines; and phosphate buffer solutions; as well as other nontoxic compatible substances used in pharmaceutical formulations. Wetting agents and lubricants, such as sodium lauryl sulphate, as well as coloring agents, flavoring agents and preservatives, can also be present.

The pharmaceutical carrier employed in conjunction with the immunomodulator imidazo[4,5-f]quinolines is used at a concentration sufficient to provide a practical size-to-dosage relationship. Preferably, the pharmaceutical carrier comprises from about 0.1% to about 99% by weight of the total composition.

Preferred dosage unit forms of the compositions of the present invention include capsules, tablets, solutions, and suspensions to be administered orally and solutions and suspensions to be administered parenterally. Preferred dosage unit forms include solutions and suspensions to be administered parenterally comprising from about 10 mg to about 500 mg of a novel immunomodulator imidazo[4,5-f]quinoline and a suitable pharmaceutical carrier; more preferred is such a dosage unit form comprising from about 50 mg to about 200 mg of such compound. Other preferred dosage unit forms include capsules and tablets each comprising from about 50 mg to about 2000 mg of a novel immunomodulator imidazo[4,5-f]quinoline and a suitable pharmaceutical carrier; more preferred is such a dosage unit form comprising from about 100 mg to about 500 mg of such compound.

While particulars embodiments of the present invention have been described, it will be obvious to those skilled in the art that various changes and modifications to the compounds and compositions disclosed herein can be made without departing from the spirit and scope of the invention. It is intended to cover, in the appended claims, all such modifications that are within the scope of this invention.

What is claimed is:

1. A compound of the class of imidazo[4,5-f]-quinolines which conform to the chemical structure or tautomeric structures thereof:

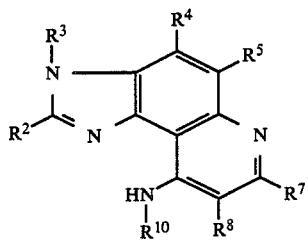

(1)

wherein $R^2$ is H, straight or branched chain lower alkyl, phenyl, substituted phenyl, furyl, thienyl, thiazoyl, or trihalomethyl; $R^3$ is H or straight or branched chain lower alkyl; $R^4$ and $R^5$ are H or straight or branched chain lower alkyl, or $R^4$ and $R^5$ are connected lower alkylene derivatives; $R^7$ is H, straight or branched chain lower alkyl, phenyl, substituted phenyl, furyl, thienyl, thiazoyl, (lower)alkoxycarbonyl, or trihalomethy; $R^8$ is H, lower alkyl, or (lower)alkoxycarbonyl, or $R^7$ and $R^8$ may join together to form a six-membered ring; and $R^{10}$ is H, straight or branched chain alkyl, cyclohexyl, methylene cyclohexyl, or unsubstituted or substituted phenyl, naphthyl, pyridyl, piperidyl, or phenylalkyl; and wherein further said substituted phenyl groups are substituted, independently, with one or more groups selected from the group consisting of halo, nitro, cyano, hydroxy, $C_1$-$C_{20}$ straight or branched chain alkyl, cyclohexyl, $C_1$-$C_{20}$ straight or branched chain alkoxy, phenyl, trifluoromethyl, phenyloxy, benzyloxy, methylene-cyclohexyloxy, cyclopentyloxy, phenylazo, piperidyl, morpholinyl, pyrrolidyl, N-methyl piperazinyl, N-benzyl piperazinyl, carboxylic acid, carboxylic acid ethyl ester, methylthio, benzoyl, acetyl, propionyl, 2-diethylamino-ethoxy, and mono- or disubstituted amines substituted with H, lower alkyl, hydroxyalkyl, and alkanoyl; except said compounds wherein $R^2$ is H or methyl or unsubstituted phenyl and $R^3=R^4=R^5=R^8=H$ and $R^7$ is H or methyl or ethyl or unsubstituted phenyl and $R^{10}$ is unsubstituted or substituted phenyl or 2-(4-methyl-1-piperazinyl)-5-pyridyl or 2-methoxy-5-pyridyl or 2-piperidino-5-pyridyl or 4-methoxybenzyl or cyclohexyl or α- or β-naphthyl; and salts and hydrates thereof.

2. A compound of the class of imidazo[4,5-f]-quinolines which conform to the chemical structure or tautomeric structures thereof:

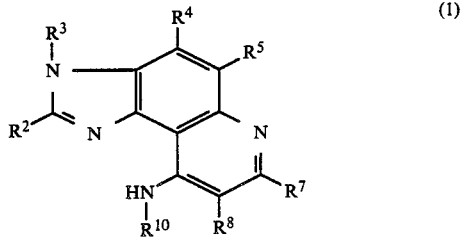

(1)

wherein $R^2$ is H, straight or branched chain lower alkyl, phenyl, substituted phenyl, furyl, thienyl, thiazoyl, or trihalomethyl; $R^3$ is H or straight or branched chain lower alkyl; $R^4$ and $R^5$ are H or straight or branched chain lower alkyl, or $R^4$ and $R^5$ are connected lower alkylene derivatives; $R^7$ is H, straight or branched chain lower alkyl, phenyl, substituted phenyl, furyl, thienyl, thiazoyl, (lower)alkoxycarbonyl, or trihalomethyl; $R^8$ is H, lower alkyl, or (lower)alkoxycarbonyl, or $R^7$ and $R^8$ may join together to form a six-membered ring; and $R^{10}$ is mono-, di- or trisubstituted phenyl; and wherein further said substituted phenyl groups are substituted, independently, with one or more groups selected from the group consisting of halo, nitro, cyano, hydroxy, $C_1$-$C_{20}$ straight or branched chain alkyl, cyclohexyl, $C_1$-$C_{20}$ straight or branched chain alkoxy, phenyl, trifluoromethyl, phenyloxy, benzyloxy, methylene-cyclohexyloxy, cyclopentyloxy, phenylazo, piperidyl, mropholinyl, pyrrolidyl, N-methyl piperazinyl, N-benzyl piperazinyl, carboxylic acid, carboxylic acid ethyl ester, methylthio, benzoyl, acetyl, propionyl, 2-diethylaminoethoxy, and mono- or disubstituted amines substituted with H, lower alkyl, hydroxyalkyl, and alkanoyl; except said compounds wherein $R^2$ is H or methyl or unsubstituted phenyl and $R^3=R^4=R^5=R^8=H$ and $R^7$ is H or methyl or ethyl or unsubstituted phenyl and $R^{10}$ is 4-methylphenyl or 2-chloro-5-methylphenyl or 4-n-butylphenyl or 3-chloro-4-methylphenyl or 4-sec-butylphenyl or 3-trifluoromethylphenyl or 3-trifluoromethyl-4-chlorophenyl or 2-phenylphenyl or 4-phenylphenyl or 2-methyl-3-chlorophenyl or 4-isopropylphenyl or 3,4-dichlorophenyl or 4-bromophenyl or 4-iodophenyl or 4-dimethylaminophenyl or 4-diethylaminophenyl or 3-chloro-4-dimethylaminophenyl or 4-piperidinophenyl or 4-(4-methylpiperazinyl)phenyl or 3-dimethylaminophenyl or 3-chloro-4-piperidinophenyl or 3-chloro-4-(4-methyl)piperazinylphenyl or 3-chloro-4-(4-benzyl)piperazinylphenyl or 4-methoxyphenyl or 4-ethoxyphenyl or 2-methoxyphenyl or 3-chloro-4-ethoxyphenyl or 4-n-butoxyphenyl or 3-methoxyphenyl or 4-phenoxyphenyl or 4-methylthiophenyl or 4-benzyloxyphenyl or 2-methylthiophenyl or 3-methylthiophenyl or 3,4-dimethoxyphenyl or 3,4-diethoxyphenyl or 3,4-diisopropoxyphenyl or 3,4-diisobutoxyphenyl or 3,4-di-n-butoxyphenyl or 3,4-disec-amyloxyphenyl or 2,5-diethoxyphenyl or 2,5-dimethoxyphenyl or 2,5- dimethoxy-4-chlorophenyl or 2-ethoxy-5-methoxyphenyl or 2-methoxy-5-ethoxyphenyl or 2,5-diethoxy-4-chlorophenyl or 2,4-dimethoxy-5-chlorophenyl or 3,4,5-trimethoxyphenyl or 2,4,5-triethoxyphenyl or 4-acetylphenyl or 3-acetylphenyl or 4-n-propionylphenyl or 4-n-butyrylphenyl or 2-methyl-4-chlorophenyl or 3-nitro-4-methylphenyl or 3-chloro-4-ethylphenyl or 3-chloro-4-n-butylphenyl or 3-chloro-4-fluorophenyl or 3-chloro-4-pyrrolidinophenyl or 4-phenylazophenyl or 2-methoxy-4-chlorophenyl or 3,4-methylenedioxyphenyl or 3,4-di-n-amyloxyphenyl or 3,4-diisoamyloxyphenyl or 4-chloro-2,5-di-n-butoxyphenyl or 4-(2-diethylamino)ethoxyphenyl, or $R^2=R^3=R^4=R^5=R^8=H$ and $R^7$ is methyl and $R^{10}$ is 4-hydroxyphenyl or 3-hydroxyphenyl or 4-acetylaminophenyl or 4-aminophenyl or 4-methylaminophenyl or 4-(1-pyrrolidinyl)phenyl or 4-(N-methyl-N-(2-hydroxyethyl)amino)phenyl or 4-carboxyphenyl or 4-chlorophenyl or 4-fluorophenyl or 4-(N-methylacetylamino)phenyl or 4-benzoylphenyl or 2-methoxy-5-acetylphenyl or 4-(2-hydroxyethyl)phenyl or 3-chlorophenyl or 4-ethylphenyl or 3-chloro-4-hydroxyphenyl or 4-morpholinophenyl or 3-chloro-4-morpholinophenyl or 4-n-dodecylphenyl or 4-carbethoxyphenyl; and salts and hydrates thereof.

3. The compound of claim 1 wherein said compound is a hydrochloride salt.

4. The compound of claim 1 wherein $R^3=R^4=R^5=R^8=H$.

5. The compound of claim 4 wherein $R^2$ is H, phenyl, furanyl, thiazoyl, or thienyl.

6. The compound of claim 5 wherein $R^7$ is H, methyl, phenyl or furanyl.

7. The compound of claim 2 wherein $R^3=R^4=R^5=R^8=H$.

8. The compound of claim 7 wherein $R^2$ is H, phenyl, furanyl, thiazoyl, or thienyl.

9. The compound of claim 8 wherein $R^7$ is H, methyl, phenyl or furanyl.

10. The compound of claim 9 wherein said substituted phenyl is substituted with halo, cyano, $C_1$-$C_{12}$ straight or branched chain alkyl, lower $C_1$-$C_{10}$ straight or branched chain alkoxy, and mono- or disubstituted amines substituted with H, lower alkyl, hydroxyalkyl, or alkanoyl.

11. The compound of claim 10 wherein said compound is a hydrochloride salt.

12. The compound according to claim 1 selected from the group consisting of 4-[[7-methyl-1H-imidazo[4,5-f]quinolin-9-yl]amino]benzonitrile hydrochloride hydrate; N-[3,4-difluorophenyl]-7-phenyl-1H-imidazole[4,5-f]quinolin-9-amine hydrochloride; N-(3,4-difluorophenyl)-1H-imidazo[4,5-f]quinolin-9-amine hydrochloride; N-[[7-phenyl-1H-imidazo[4,5-f]quinolin-9-yl]amino]-benzonitrile hydrochloride hydrate; and 2-(2-furanyl)-N-(4-methoxyphenyl)-7-methyl-1H-imidazo[4,5-f]quinolin-9-amine hydrochloride hydrate.

13. A method for enhancing the immune response system of a mammal which comprises systematically administering to a mammal having a depressed immune function a pharmaceutical composition comprising a compound conforming to the following chemical structure or tautomeric structures thereof:

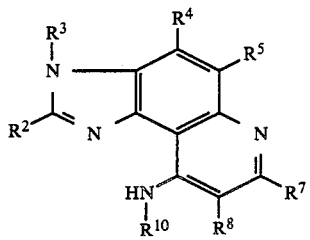

(1)

wherein $R^2$ is H, straight or branched chain lower alkyl, phenyl, substituted phenyl, furyl, thienyl, thiazoyl, or trihalomethyl; $R^3$ is H or straight or branched chain lower alkyl; $R^4$ and $R^5$ are H or straight or branched chain lower alkyl, or $R^4$ and $R^5$ are connected lower alkylene derivatives; $R^7$ is H, straight or branched chain lower alkyl, phenyl, substituted phenyl, furyl, thienyl, thiazoyl, (lower)alkoxycarbonyl, or trihalomethyl; $R^8$ is H, lower alkyl, or (lower)alkoxycarbonyl, or $R^7$ and $R^8$ may join together to form a six-membered ring; and $R^{10}$ is H, straight or branched chain alkyl, cyclohexyl, methylene cyclohexyl, or unsubstituted or substituted phenyl, naphthyl, pyridyl, piperidyl, or phenylalkyl; and salts and hydrates thereof; and wherein further said substituted phenyl groups are substituted, independently, with one or more groups selected from the groups consisting of halo, nitro, cyano, hydroxy, $C_1$-$C_{20}$ straight or branched chain alkyl, cyclohexyl, $C_1$-$C_{20}$ straight or branched chain alkoxy, phenyl, trifluoromethyl, phenyloxy, benzyloxy, methylenecyclohexyloxy, cyclopentyloxy, phenylazo, piperidyl, morpholinyl, pyrrolidyl, N-methyl piperazinyl, N-benzyl piperazinyl, carboxylic acid, carboxlic acid ethyl ester, methylthio, benzoyl, acetyl, propionyl, 2-diethylamino-ethoxy, and mono- or disubstituted amines substituted with H, lower alkyl, hydroxyalkyl, and alkanoyl; said pharmaceutical composition being administered to said mammal in an amount which is non-toxic but which is effective to enhance the function of the immune response system of said mammal.

14. The method of claim 13 wherein $R^{10}$ is selected from unsubstituted phenyl and mono-, di- or trisubstituted phenyl; and $R^3=R^4=R^5=R^8=H$.

15. The method of claim 14 wherein $R^2$ is H, phenyl, furanyl, thiazoyl, or thienyl; and $R^7$ is H, methyl, phenyl or furanyl.

16. The method of claim 15 wherein said substituted phenyl is substituted with halo, cyano, $C_1$-$C_{12}$ straight or branched chain alkyl, lower $C_1$-$C_{10}$ straight or branched chain alkoxy, and mono- or disubstituted amines substituted with H, lower alkyl, hydroxyalkyl, or alkanoyl.

17. The method of claim 16 wherein said compound is a hydrochloride salt.

18. The method of claim 13 wherein said compound is selected from the group consisting of 4-[[7-methyl-1H-imidazo[4,5-f]quinolin-9-yl]amino]benzonitrile hydrochloride hydrate; N-[3,4-difluorophenyl]-7-phenyl-1H-imidazo[4,5-f]quinolin-9amine hydrochloride; N-(3,4-difluorophenyl)-1H-imidazo[4,5-f]quinolin-9-amine hydrochloride; 4-[[7-phenyl-1H-imidazo[4,5-f]quinoline-9-yl]amino]benzonitrile hydrochloride hydrate; 2-(2-furanyl)-N-(4-methoxyphenyl)-7-1H-imidazo[4,5-f]-quinolin-9-amine hydrochloride hydrate; 9-[p-(N-methylacetamido)anilino]-7-methyl-1H-imidazo[4,5-f]quinoline hydrochloride hydrate; 9-(p-anisidino)-7- methyl-2-phenyl-1H-imidazo[4,5-f]quinoline hydrochloride hydrate; and 9-(p-butylanilino)-7-phenyl-1H-imidazo[4,5-f]quinoline hyrochloride.

19. A pharmaceutical composition in dosage unit form for enhancing the immune response system of a mammal comprising:
   (1) a nontoxic amount of the compound of claim 1, which nontoxic amount is effective to enhance the function of the immune response system of said mammal; and
   (2) a pharmaceutical carrier.

20. A pharmaceutical composition in dosage unit form for enhancing the immune response system of a mammal comprising:
   (1) a nontoxic amount of the compound of claim 2, which nontoxic amount is effective to enhance the function of the immune response system of said mammal; and
   (2) a pharmaceutical carrier.

21. A pharmaceutical composition in dosage unit form for enhancing the immune response system of a mammal comprising:
   (1) a nontoxic amount of the compound of claim 12, which nontoxic amount is effective to enhance the function of the immune response system of said mammal; and
   (2) a pharmaceutical carrier.

* * * * *